(12) United States Patent
Butters et al.

(10) Patent No.: US 8,034,932 B2
(45) Date of Patent: Oct. 11, 2011

(54) CHEMICAL PROCESS

(75) Inventors: Michael Butters, Bristol (GB); Steven Robert Lenger, Bristol (GB); Paul Michael Murray, Bristol (GB); Evan William Snape, Bristol (GB)

(73) Assignee: AstraZeneca UK Limited, London (GB)

( * ) Notice: Subject to any disclaimer, the term of this patent is extended or adjusted under 35 U.S.C. 154(b) by 699 days.

(21) Appl. No.: 11/793,418

(22) PCT Filed: Dec. 22, 2005

(86) PCT No.: PCT/GB2005/004999
§ 371 (c)(1),
(2), (4) Date: Jun. 20, 2007

(87) PCT Pub. No.: WO2006/067456
PCT Pub. Date: Jun. 29, 2006

(65) Prior Publication Data
US 2008/0207903 A1    Aug. 28, 2008

(30) Foreign Application Priority Data
Dec. 24, 2004   (GB) .................................. 0428328.9

(51) Int. Cl.
*C07D 239/36* (2006.01)
*C07D 239/42* (2006.01)
(52) U.S. Cl. .................. 544/330; 544/331; 544/332
(58) Field of Classification Search .................. 544/330, 544/331, 332
See application file for complete search history.

(56) References Cited

U.S. PATENT DOCUMENTS

| | | |
|---|---|---|
| 4,613,610 A | 9/1986 | Wareing |
| 4,625,039 A | 11/1986 | Jewell, Jr. et al. |
| 4,645,858 A | 2/1987 | Lowrie et al. |
| 4,650,890 A | 3/1987 | Jewell, Jr. et al. |
| 4,677,211 A | 6/1987 | Jewell, Jr. et al. |
| 480,621 A | 2/1989 | Roth et al. |
| 4,957,971 A | 9/1990 | Picard et al. |
| 4,968,681 A | 11/1990 | Hubsch et al. |
| 4,970,313 A | 11/1990 | Wess et al. |
| 4,977,279 A | 12/1990 | Wess et al. |
| 5,079,347 A | 1/1992 | Buch |
| 5,102,893 A | 4/1992 | Picard et al. |
| 5,260,440 A | 11/1993 | Hirai et al. |
| 5,278,313 A | 1/1994 | Thottathil et al. |
| 5,399,722 A | 3/1995 | Beck et al. |
| 5,594,153 A | 1/1997 | Thottathil et al. |
| 5,681,957 A | 10/1997 | Wolters et al. |
| 6,278,001 B1 | 8/2001 | Solladie et al. |
| 6,331,641 B1 | 12/2001 | Taoka et al. |
| 6,579,984 B1 | 6/2003 | Veith |
| 6,689,591 B2 | 2/2004 | Muller et al. |
| 6,784,171 B2 | 8/2004 | Taylor et al. |
| 6,844,437 B1 | 1/2005 | Taylor et al. |
| 6,855,716 B2 | 2/2005 | Ohno et al. |
| 6,870,059 B2 | 3/2005 | Kooistra et al. |
| 7,157,255 B2 | 1/2007 | Blacker et al. |
| 7,199,140 B2 | 4/2007 | Hayter et al. |
| 7,304,156 B2 | 12/2007 | Matsushita et al. |
| 7,416,865 B2 | 8/2008 | Blacker et al. |
| 7,442,811 B2 | 10/2008 | Bakel Van et al. |
| 7,511,140 B2 | 3/2009 | Horbury et al. |
| 7,524,955 B2 | 4/2009 | Newton et al. |
| 7,642,363 B2 | 1/2010 | Kooistra et al. |
| 7,718,812 B2 | 5/2010 | Hof ............................. 549/333 |
| 7,732,171 B2 | 6/2010 | Blacker et al. ................. 435/135 |
| 7,816,528 B2 | 10/2010 | Matsushita et al. ........... 544/315 |
| 2003/0018199 A1 | 1/2003 | Brodfuehrer et al. |
| 2005/0124639 A1 | 6/2005 | Joshi et al. |
| 2006/0293355 A1 | 12/2006 | Booth et al. ................... 514/275 |
| 2007/0093660 A1 | 4/2007 | Tararov et al. |
| 2007/0105882 A1 | 5/2007 | Black et al. .................... 514/275 |

(Continued)

FOREIGN PATENT DOCUMENTS

EP    0 252 476    1/1988

(Continued)

OTHER PUBLICATIONS

Watanabe, M., et al.: "Synthesis and Biological Activity of Methanesulfonamide Pyrimidine-And N-Methanesulfonyl Pyrrole-Substituted 3,5-Dihydroxy-6-heptenoates, A Novel Series of HMG-CoA Reductase Inhibitors", Bioorganic & Medicinal Chemistry, vol. 5(2), pp. 437-444, 1997.

(Continued)

*Primary Examiner* — Venkataraman Balasubramanian
(74) *Attorney, Agent, or Firm* — Morgan Lewis & Bockius LLP

(57) ABSTRACT

A process for formation of a compound of formula (I) or a pharmaceutically acceptable salt thereof, (A chemical formula should be inserted here—please see paper copy enclosed herewith) I via a Heck reaction is described. Intermediates useful in the process and processes for making said intermediates are also described.

(I)

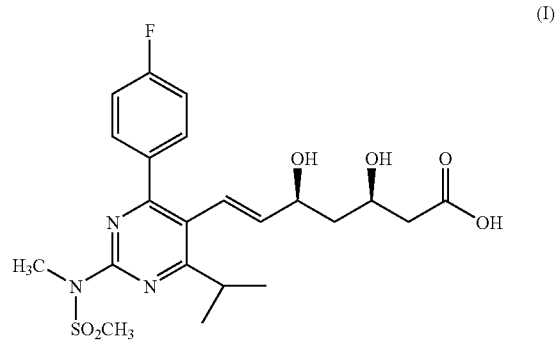

12 Claims, No Drawings

U.S. PATENT DOCUMENTS

| | | | |
|---|---|---|---|
| 2007/0255060 A1 | 11/2007 | Okada et al. | 544/297 |
| 2008/0188657 A1 | 8/2008 | Lenger | 544/297 |
| 2008/0221323 A1 | 9/2008 | Crabb et al. | 544/297 |
| 2009/0264654 A1 | 10/2009 | Newton et al. | 544/331 |
| 2009/0286819 A1 | 11/2009 | Horbury et al. | 514/275 |
| 2010/0222373 A1 | 9/2010 | Booth et al. | 514/275 |
| 2010/0228028 A1 | 9/2010 | Butters et al. | 544/297 |

FOREIGN PATENT DOCUMENTS

| | | |
|---|---|---|
| EP | 0319845 | 6/1989 |
| EP | 0319847 | 6/1989 |
| EP | 0521471 | 10/2000 |
| GB | 2244705 | 12/1991 |
| JP | 06256318 | 9/1994 |
| WO | WO 90/03973 | 4/1990 |
| WO | WO 92/01675 | 2/1992 |
| WO | WO 93/08823 | 5/1993 |
| WO | WO 96/14846 | 5/1996 |
| WO | WO 97/19917 | 6/1997 |
| WO | WO 97/21687 | 6/1997 |
| WO | WO 99/07695 | 2/1999 |
| WO | WO 00/49014 | 8/2000 |
| WO | WO 00/78730 | 12/2000 |
| WO | WO 01/04100 | 1/2001 |
| WO | WO 01/04336 | 1/2001 |
| WO | WO 01/60804 | 8/2001 |
| WO | WO 01/72706 | 10/2001 |
| WO | WO 01/85702 | 11/2001 |
| WO | WO 01/85975 | 11/2001 |
| WO | WO 02/05519 | 1/2002 |
| WO | WO 02/06266 | 1/2002 |
| WO | 02/38551 | 5/2002 |
| WO | WO 03/004450 | 1/2003 |
| WO | WO 03/006439 | 1/2003 |
| WO | WO 03/018555 | 3/2003 |
| WO | WO 03/059901 | 7/2003 |
| WO | WO 03/064382 | 8/2003 |
| WO | WO 03/087112 | 10/2003 |
| WO | WO 03/106447 | 12/2003 |
| WO | WO 2004/014872 | 2/2004 |
| WO | WO 2004/052867 | 6/2004 |
| WO | WO 2004/054986 | 7/2004 |
| WO | WO 2004/103977 | 12/2004 |
| WO | WO 2004/108691 | 12/2004 |
| WO | WO 2005/023779 | 3/2005 |
| WO | WO 2005/028450 | 3/2005 |
| WO | WO 2005/042522 | 5/2005 |
| WO | WO 2005/047276 | 5/2005 |
| WO | WO 2005/063728 | 7/2005 |
| WO | WO 2006/067456 | 6/2006 |
| WO | WO 2006/089401 | 8/2006 |
| WO | WO 2007/007119 | 1/2007 |

OTHER PUBLICATIONS

Hannah, D. R., et al.: "Structural Studies on Bioactive Compounds. Part 29: Palladium Catalysed Arylations and Alkynylations of Sterically Hindered Immunomodulatory 2-Amino-5-halo-4,6-(Disubstituted) pyrimidines", Bioorganic & Medicinal Chemistry, vol. 8(4), pp. 739-750, 2000.

Hauser, C. R., et al.: "Synthesis of 5-Phenyl-4,6-Pyrimidol and Derivatives from the Cyclization of Urea with 3-Phenyl-2,4-Pentanedione", Journal of Organic Chemistry, American Chemical Society, vol. 18, pp. 588-593, 1953.

Breaux et al. "An Improved General Synthesis of 4-Aryl-5-Pyrimidinecarboxylates" J. Heterocyclic Chem. 18: 183 (1981).

De Luca et al. "Cellulose Beads: a New Versatile Solid Support for Microwave-Assisted Synthesis. Preparation of Pyrazole and Isoxazole Libraries" J. Comb. Chem. 5(4):465-471 (2003).

Grohe et al. "Synthese and Reaktionen von 2,4-Dichlorpyrimidin-5-carbon-saureestem" Liebigs Ann. Chem. 1025-1035 (1973).

Hannah et al. "Structural studies on bioactive compounds. Part 29: palladium catalysed arylations and alkynylations of sterically hindered immunomodulatory 2-amino-5-halo-4,6-(disubstituted)pyrimidines" Bioorg Med Chem. 8(4):739-750 (2000).

Hauser et al. "Synthesis of 5-phenyl-4,6-dimethyl-2-pyrimidol and derivatives from the cyclization of urea with 3-phenyl-2,4-pentanedione" Journal of Organic Chemistry 18(5): 588-593 (1953).

Hiyama et al. "Synthesis of Artificial HMG-CoA Reductase Inhibitors Based on the Olefination Strategy" Bull. Chem. Soc. Jpn. 68 (1):364-372 (1995).

Kaneko et al. "Preparation of optically active 5,6-epoxyhexanoic acid esters as materials for physiologically active substances" Chemical Abstracts + Indexes, American Chemical Society, Columbus, US 118(11):832 (1993).

Ma et al. "Lanthanide triflate catalyzed Biginelli reaction. One pot synthesis of dihydropyrimidinones under solvent-free condition" J. Org. Chem. 65:3864-3868 (2000).

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

Minami et al. "A Novel Enantioselective Synthesis of HMG Co-A Reductase Inhibitor NK-104 and a Related Compound" Tetrahedron letters 33(49):7525-7526 (1992).

Minami et al. "Stereoselective Reduction of β,δ-Diketo Esters Derived From Tartaric Acid. A Facile Route to Optically Active 6-oxo-3,5-syn-isopropylidenedioxyhexanoate, a Versatile Synthetic Intermediate of Artificial HMG Co-A Reductase Inhibitors" Tetrahedron Letters 34(3):513-516 (1993).

Prasad et al. "A novel diastereroselective synthesis of lactone moiety of compactin" Tetrahedron Letters 25(23):2435-2438 (1984).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Sakaki et al. "Lipase-catalyzed asymmetric synthesis of 6-(3-chloro-2-hydroxypropyl)-1,3-dioxin-4-ones and their conversion to chiral 5,6-epoxyhexanoates" Tetrahedron: Asymmetry 2(5):343-346 (1991).

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

Solladié et al. "Chrial Sulfoxides in Asymmetric Synthesis: Enantioselective Synthesis of the Lactonic Moiety of (+)-Compactin and (+)-Mevinolin. Application of a Compactin Analogue" J. Org. Chem. 60:7774-7777 (1995).

Vanden Eynde et al. "Microwave-mediated Regioselective Synthesis of. Novel Pyrimido[1,2-a]pyrimidines under Solvent-free Conditions" Tetrahedron 57(9):1785-1791 (2001).

Watanabe et al. "Synthesis and Biological Activity of Methanesulfonamide Pyrimidine- and N-Methanesulfonly Pyrrole-Substituted 3,5-Dihydroxy-6-heptenoates, a Novel Series of HMG-CoA Reductase Inhibitors" Biord. Med. Chem. 5(2):437-444 (1997).

Wess et al. "Stereoselective Synthesis of HR 780 A New Highly Potent HMG-CoA Reductase Inhibitor", Tetrahedron Letters 31(18): 2545-2548 (1990).

Moore et al. "Biosynthesis of the hypocholesterolemic agent mevinolin by Aspergillus terreus. Determination of the origin of carbon, hydrogen, and oxygen atoms by carbon-13 NMR and mass spectrometry" J. Am. Chem. Soc. 107(12): 3694-3701 (1985).

Anne et al. "Enantioselective synthesss of key A-ring precursors of 1α, 25-dihydroxyvitamin $D_3$ and analogues" Synlett 9:1435-1437 (1999).

Bhaskar Reddy et al. "Enantioselective synthesis of β-hydroxy δ-lactones: a new approach to the synthetic congeners of 3-hydroxy-3-methylglutaryl coenzyme A reductase inhibitors" J. Org. Chem. 56(20):5752-5754 (1991).

Blandin et al. "One-pot and sequential asymmetric hydrogenation of β,δ-diketoesters into functionalized 1,3-diols: From anti- to syn-stereoselectivity" European Journal of Organic Chemistry 12:3421-3427 (1999).

BouzBouz et al. "Regioselective Cross-Metathesis Reaction Induced by Steric Hindrance" Organic Letters 6(20):3465-3467 (2004).

Bovy et al. "Synthesis of Heterocyclic β-Amino Acids. A convenient preparation of β-Amino-5-pyrimidinepropanoic acid and derivatives" Tetrahedron Letters 34(50):8015-8018 (1993).

Casini et al. "Carbonic anhydrase inhibitors with strong topical antiglaucoma properties incorporating a 4-(2-amino-pyrimidin-4-yl-amino)-benzenesulfonamide scaffold" Journal of Enzyme Inhibition and Medicinal Chemistry 17(1):9-18 (2002).

Castro et al. "A new synthesis of 3,5-dihydroxy-7-(1-pyrroly1)-6-heptenoic acids. A family of HMGCoA reductase inhibitors with antifungal activity" Tetrahedron Letters 43:1851-1854 (2002).

Denmark et al. "The Chemistry of Trichlorosilyl Enolates. Aldol Addition Reactions of Methyl Ketones" J. Am. Chem. Soc. 122 (37):8837-8847 (2000).

Dovlatyan et al. "Studies on functionally-substituted azines. 8. Synthesis and transformations of 1-arylsulfonylamido-4-methoxy-6-methylpyrimidines" Chemistry of Heterocyclic Compounds 36(11):1306-1313(2000).

Evans et al. "Diastereoselective synthesis of protected syn 1,3-diols by base-catalyzed intramolecular conjugate addition of hemiacetal-derived alkoxide nucleophiles" J. Org. Chem. 58:2446-2453 (1993).

Feuerstein et al. "A new efficient tetraphosphine/palladium catalyst for the Heck reaction of aryl halides with styrene or vinylether derivatives" Tetrahedron Letters 43:2191-2194 (2002).

Gu et al. "Synthesis of ent-Haterumalide NA (ent-Oocydin A) Methyl Ester" Organic Letters 5(23):4385-4388 (2003).

Littke et al. "A Versatile Catalyst for Heck Reactions of Aryl Chlorides and Aryl Bromides under Mild Conditions" J. Am. Chem. Soc. 123(29):6989-7000 (2001).

Littke et al. "Heck reactions in the presence of P($t$-Bu)$_3$: Expanded scope and milder reaction conditions for the coupling of aryl chlorides" J. Org. Chem. 64:10-11 (1999).

Miller et al. "Discovery of Aminopyridine-Based Inhibitors of Bacterial Enoyl-ACP Reductase (FabI)" J. Med. Chem. 45(15):3246-3256 (2002).

Mohr et al. "Stereoselective synthesis of functionalized erythro/1,3-diols" Tetrahedron Letters 28(4):391-394 (1987).

Scialdone et al. "Building blocks for skipped polyols: syn-1,3-acetonides by chemoenzymatic synthesis from cycloheptatriene" Tetrahedron Letters 36(1):43-46 (1995).

Singer et al. "Catalytic, enantioselective dienolate additions to aldehydes: Preparation of optically-active acetoacetate aldol adducts" Journal of the American Chemical Society 117(49):12360-12361 (1995).

Takahashi et al. "Synthesis of an artificial HMG-CoA reductase inhibitor NK-104 via a hydrosilylation-cross-coupling reaction" Bulletin of the Chemical Society of Japan 68(9):2649-2656 (1995).

Virolleaud et al. "A straightforward synthesis of ($E$)-δ-alkenyl-β,γ-unsaturated δ-lactones by a tandem ring-closing/cross-coupling metathesis process" Tetrahedron Letters 44(44):8081-8084 (2003).

Zakrzewski et al. "Synthesis of syn- and anti-3,5-Dihydroxy-6-heptenoates from 2-Deoxy-d-ribose: Intermediates for Polyols Synthesis" Synlett 2:215-218 (2003).

Beletskaya et al., "The heck reaction as a sharpening stone of palladium catalysis," Chem. Rev., 2000 100(8);3009-3066.

European Examination Report for European Application No. 05820940.4 dated Mar. 28, 2011.

CHEMICAL PROCESS

This invention concerns a novel chemical process, and more particularly it concerns a novel chemical process for the manufacture of rosuvastatin and its pharmaceutically acceptable salts, especially rosuvastatin calcium, as well novel intermediates used in said process and processes for the manufacture of the novel intermediates.

Rosuvastatin and its pharmaceutically acceptable salts are HMG CoA reductase inhibitors and have use in the treatment of, inter alia, hypercholesterolemia and mixed dyslipidemia. Rosuvastatin calcium is marketed under the trademark CRESTOR™. European Patent Application, Publication No. (EPA) 0521471 discloses (E)-7-[4-(4-fluorophenyl)-6-isopropyl-2-[methyl(methylsulfonyl)amino]pyrimidin-5-yl] (3R,5S)-3,5-dihydroxyhept-6-enoic acid (rosuvastatin) and its sodium salt and calcium salt (rosuvastatin calcium, illustrated below) and a process for their preparation.

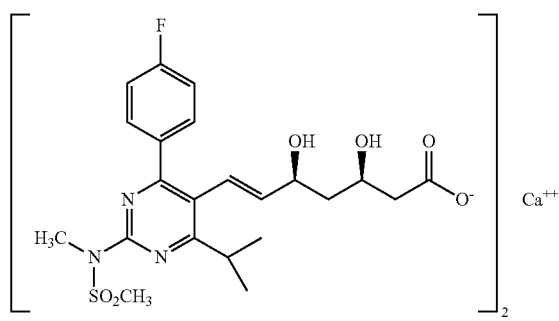

Rosuvastatin and its pharmaceutically acceptable salts are obtained therein by condensation of methyl (3R)-3-[(tert-butyldimethylsilyl)oxy]-5-oxo-6-triphenylphosphoranylidene hexanoate with 4-(4-fluorophenyl)-6-isopropyl-2-(N-methyl-N-methanesulfonylamino)-5-pyrimidinecarboxaldehyde, followed by deprotection of the 3-hydroxy group, asymmetric reduction of the 5-oxo group and hydrolysis.

Other processes for the preparation of rosuvastatin and its pharmaceutically acceptable salts are described in WO 00/49014 and WO 04/52867. The compound and its pharmaceutically acceptable salts are obtained in WO 00/49104 by reaction of diphenyl[4-(4-fluorophenyl)-6-isopropyl-2-[methyl(methylsulfonyl)amino]pyrimidin-5-ylmethyl]phosphine oxide with tert-butyl 2-[(4R,6S)-6-formyl-2,2-dimethyl-1,3-dioxan-4-yl}acetate in the presence of a base, followed by removal of protecting groups. WO 04/52867 discloses the condensation of 1-cyano-(2S)-2-[(tert-butyldimethylsilyl)oxy-4-oxo-5-triphenylphosphoranylidene pentane with 4-(4-fluorophenyl)-6-isopropyl-2-(N-methyl-N-methanesulfonylamino)-5-pyrimidinecarboxaldehyde, followed by deprotection, asymmetric reduction of the 4-oxo group and hydrolysis.

However there is a continuing need to identify alternative processes for the manufacture of rosuvastatin and its pharmaceutically acceptable salts. Such processes may, for example, when compared to previously known processes, be more convenient to use, be more suitable for large scale manufacture, give the product in a better yield, reduce the number of steps involved, use intermediates which are more easily isolated, require less complex purification techniques, use less expensive reagents and/or be more environmentally friendly.

WO 03/004450 (Ciba Specialty Chemicals) discloses a process for preparation of heptanoic acid derivatives and their use as intermediates in the synthesis of statin derivatives. WO 03/018555 (Ciba Specialty Chemicals) discloses a process for preparation of indole derivatives, such as fluvastatin. EP252476 (Warner Lambert) discloses compounds which are HMG CoA reductase inhibitors and a process for their synthesis.

We have now discovered a particularly useful process for preparing rosuvastatin and its pharmaceutically acceptable salts.

According to a first aspect of the invention, there is provided a process for the manufacture of a compound of formula I

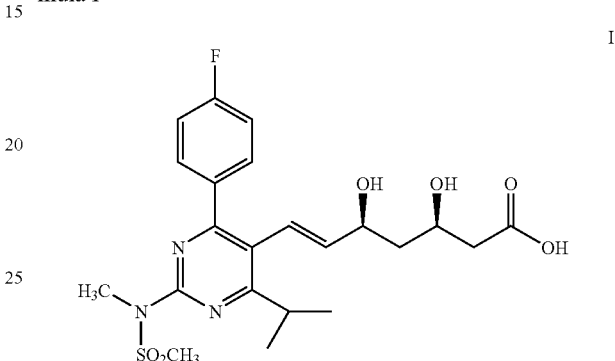

or a pharmaceutically acceptable salt thereof,
which comprises reaction of a compound of formula II,

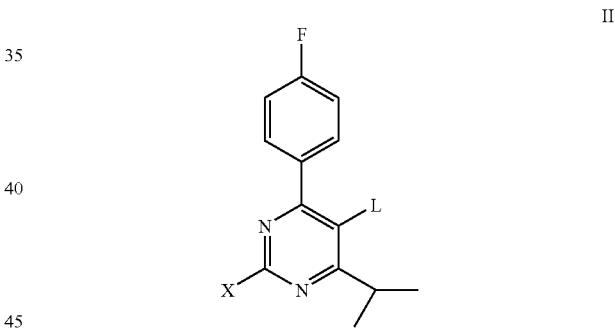

wherein L is a leaving group and X is a group Z which is N-(methyl)methylsulfonylamino ($CH_3SO_2N(CH_3)$—) or X is a group Y which is a group that is capable of conversion into the group Z,
with a compound of the formula III,

wherein
A is selected from a group (i) to (vii) below,

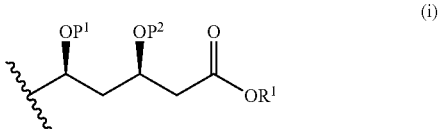

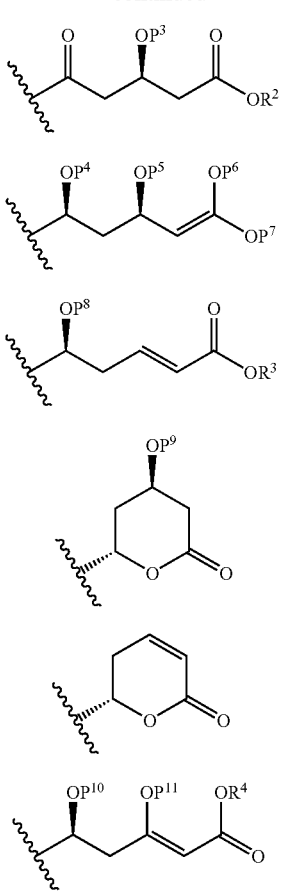

wherein $P^1$ and $P^2$ are independently selected from hydrogen and a hydroxy protecting group, or $P^1$ together with $P^2$ form a 1,3-dihydroxy protecting group;
$P^3$ is hydrogen or a hydroxy protecting group;
$P^4$ and $P^5$ are independently selected from hydrogen and a hydroxy protecting group, or $P^4$ together with $P^5$ form a 1,3-dihydroxy protecting group, and $P^6$ and $P^7$ are independently a hydroxy protecting group; or $P^5$ together with $P^6$ form a 1,3-dihydroxy protecting group, and $P^4$ is hydrogen or a hydroxy protecting group and $P^7$ is a hydroxy protecting group;
$P^8$ is hydrogen or a hydroxy protecting group;
$P^9$ is hydrogen or a hydroxy protecting group;
$P^{10}$ and $P^{11}$ are independently selected from hydrogen and a hydroxy protecting group, or $P^{10}$ together with $P^{11}$, or $P^{11}$ together with $R^4$, form a 1,3-dihydroxy protecting group; and unless otherwise stated $R^1$, $R^2$, $R^3$ and $R^4$ are independently carboxy protecting groups;
in the presence of a catalytically effective amount of a palladium catalyst and in the presence of a base;
followed by
(a) when X is a group Y, the group Y is converted into the group Z; followed by
(b) when A is a group (i), carrying out in any order the steps of (1) when $P^1$ is a hydroxy protecting group, removal of the protecting group $P^1$; (2) when $P^2$ is a hydroxy protecting group, removal of the protecting group $P^2$; and (3) removal of the protecting group $R^1$;
(c) when A is a group (ii), carrying out in any order the steps of (1) asymmetric reduction of the carbonyl group adjacent to the carbon-carbon double bond; (2) when $P^3$ is a hydroxy protecting group, removal of the protecting group $P^3$; and (3) removal of the protecting group $R^2$;
(d) when A is a group (iii), carrying out in any order the steps of (1) when $P^4$ is a hydroxy protecting group, removal of the protecting group $P^4$; (2) when $P^5$ is a hydroxy protecting group, removal of the protecting group $P^5$; (3) removal of the protecting group $P^6$; and (4) removal of the protecting group $P^7$;
(e) when A is a group (iv), carrying out in any order the steps of (1) when $P^8$ is a hydroxy protecting group, removal of the protecting group $P^8$; (2) asymmetric hydration of the carbon-carbon double bond adjacent to the ester group $COOR^3$; and (3) removal of the protecting group $R^3$;
(f) when A is a group (v), carrying out in any order the steps of (1) when $P^9$ is a hydroxy protecting group, removal of the protecting group $P^9$; and (2) hydrolysis under basic conditions;
(g) when A is a group (vi), carrying out in any order the steps of (1) asymmetric hydration of the ring carbon-carbon double bond; and (2) hydrolysis under basic conditions; and
(h) when A is a group (vii), carrying out in any order the steps of (1) asymmetric reduction of the carbon-carbon double bond adjacent to the group $COOR^4$; (2) when $P_{10}$ is a hydroxy protecting group, removal of the protecting group $P^{10}$; (3) when $P^{11}$ is a hydroxy protecting group, removal of the protecting group $P^{11}$; and (4) removal of the protecting group $R^4$;
whereafter, when the product is obtained in the free acid form, optionally forming a pharmaceutically acceptable salt of the compound of formula I, or when the product is obtained as a salt, optionally converting the product to a different pharmaceutically acceptable salt.

For the avoidance of doubt, the carbon atom bearing the group $OP^1$ in the group A(i) is attached directly to the carbon-carbon double bond of formula III, and the groups A(ii) to A(vii) are attached in a likewise manner.

It will be appreciated that tautomeric forms of the groups A are also included within the scope of the present invention. For example, when A is a group (vii) in which $P^{11}$ is hydrogen, this may exist in the keto form shown below.

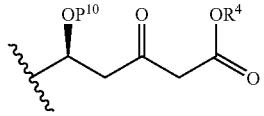

Suitable palladium catalysts are, for example, those disclosed in J. Am. Chem. Soc., 2001, 123, 6989-7000 (which reference and more particularly the palladium catalysts described therein are hereby incorporated herein by reference), and analogous palladium catalysts, for carrying out the so-called Heck reaction. Although the Heck reaction is well known in the art for coupling certain aryl and heteroaryl halides (or triflates or acid chlorides) with alkenes, it has surprisingly been found that the Heck reaction can be carried out with a fully substituted, sterically-hindered 6-membered pyrimidine of formula II.

Particularly suitable palladium catalysts include, for example, those with trialkylphosphine ligands (Pd/P(alkyl)$_3$), especially bis(tri-tert-butylphosphine)palladium (0). A Pd/P(alkyl)$_3$ catalyst wherein the alkyl group is tert-butyl, such as a mixture of Pd$_2$(dba)$_3$ and P(t-Bu)$_3$, may also be used.

The term "catalytically effective amount" means an amount from 1 mol % to 30 mol %, particularly from 2 mol % to 20 mol %, and more particularly from 5 mol % to 10 mol %, based on the amount of the compound of formula II.

The compounds of formula II and III are generally reacted together in the ratio of about 1 to 1.

Generally the reaction is carried out in a suitable solvent such as toluene, diphenyl ether and poly(ethylene glycol), and particularly N,N-dimethylformamide, N-methylpyrrolidone, N,N-dimethylacetamide, or dimethylsulfoxide, and more particularly water and binary mixtures of water and N,N-dimethylformamide and N,N-dimethylacetamide.

Generally the reaction is carried out at a temperature in the range 30-110° C., particularly 40-80° C., more particularly 50-60° C.

Suitable bases for use in the process of the invention include, for example, amine bases, such as ammonia, and particularly bulky tertiary amines such as N-methyldicyclohexylamine, used either stoichiometrically or catalytically with a stoichiometric amount of an inorganic base, such as cesium carbonate.

The reaction may also optionally be carried out in the presence of a tetrabutylammonium salt, such as tetrabutylammonium chloride or tetrabutylammonium tetrafluoroborate.

Particularly combinations of palladium catalyst, solvent and base (optionally in the presence of a tetrabutylammonium salt), which are suitable for carrying out the process of the invention, include the following:
Bis(tri-tert-butylphosphine)palladium (0), water, N,N-dicyclohexylmethylamine;
Bis(tri-tert-butylphosphine)palladium (0), water, N,N-dicyclohexylmethylamine, tetrabutylammonium chloride;
Bis(tri-tert-butylphosphine)palladium (0), water, N,N-dicyclohexylmethylamine, tetrabutylammonium tetrafluoroborate;
Bis(tri-tert-butylphosphine)palladium (0), toluene, N,N-dicyclohexylmethylamine, tetrabutylammonium chloride;
Bis(tri-tert-butylphosphine)palladium (0), N,N-dimethylacetamide, N,N-dicyclohexylmethylamine, tetrabutylammonium chloride;
Bis(tri-tert-butylphosphine)palladium (0), water/DMF (1:1), N,N-dicyclohexylmethylamine,
Bis(tri-tert-butylphosphine)palladium (0), water/DMF (1:1), N,N-dicyclohexylmethylamine, tetrabutylammonium chloride; and
Bis(tri-tert-butylphosphine)palladium (0), water/DMF (1:1), ammonia.

A leaving group L referred to hereinbefore or hereinafter includes, for example, chloro, bromo, iodo, —OSO$_2$CF$_3$, —COCl, —SO$_2$Cl and —C(O)O—SO$_2$R$^y$ wherein R$^y$ is aryl (such as phenyl) or substituted aryl (such as tolyl), particularly chloro, bromo, iodo, —OSO$_2$CF$_3$, and more particularly bromo.

The term "a group that is capable of conversion into a group Z" means that the group Y is selected from any functional group which can be converted, by carrying out one or more synthetic chemical steps, to form the group Z. Suitable groups Y which are capable of such conversion, and the synthetic chemical steps that can be used to carry out the conversion of Y into Z, are well known in the art, for example as described in standard works such as Contemporary Heterocyclic Chemistry by George R. Newkome and William W. Paudler, published by John Wiley & Sons, Inc., and Advanced Organic Chemistry by J. March, 4$^{th}$ and 5$^{th}$ Editions. Typical groups Y and synthetic chemical steps suitable for such conversion are illustrated, for example, in any of Schemes 1 to 5 or in the examples hereinafter, or by analogy therewith.

A group Y referred to hereinbefore or hereinafter includes, for example, hydroxy, chloro, bromo, iodo, amino, methylamino, benzylamino, methanesulfonylamino, N-benzylmethanesulfonylamino, R$^x$SO$_2$O— wherein R$^x$ is (1-6C) alkyl (such as methyl, ethyl or propyl), aryl (such as phenyl) or substituted aryl (such as tolyl), R$^y$C(O)O— wherein R$^y$ is (1-6C)alkyl (such as methyl, ethyl or propyl), aryl (such as phenyl) or substituted aryl (such as tolyl). Particularly suitable groups Y include, for example, hydroxy, chloro, tosyloxy, amino, methylamino and methylsulfonylamino.

The term "aryl" herein includes, for example, a monocyclic or bicyclic aromatic hydrocarbon group that contains 6-12 atoms, such as phenyl, naphthyl, tetrahydronaphthyl, indenyl and indanyl, particularly phenyl. The term "substituted aryl" means an aryl group bearing one or more substituents, for example 1 to 3 substituents, more particularly 1 to 2 substituents. Suitable substituents include, for example, (1-4C)alkyl (such as methyl, ethyl or propyl), (1-4C)alkoxy (such as methoxy or ethoxy) and halogeno (such as chloro, bromo or iodo).

The terms "hydroxy protecting group" and "carboxy protecting group" referred to hereinbefore or hereinafter mean that the hydroxy or carboxy group is protected from reaction by forming a suitable derivative, such as a (1-4C)alkyl ester group. A hydroxy protecting group also includes, for example, tetrahydropyranyl, tert-butyl, methoxymethyl or a silyl radical, for example a silyl radical of the formula SiR$_3$ wherein the R radicals can be the same or different and are selected from (1-6C)alkyl, phenyl and phenyl(1-4C)alkyl, in which latter two groups a phenyl group is unsubstituted or bears a halogeno, (1-4C)alkoxy or (1-4C)alkyl substituent. For example, a group SiR$_3$, includes trimethylsilyl and tert-butyldimethylsilyl. Examples of suitable means of protection of hydroxy and carboxy groups (as well as means of formation and eventual deprotection), may be found in T. W. Greene and P. G. M. Wuts, "Protective Groups in Organic Synthesis", Third Edition, John Wiley & Sons, New York, 1999. Particular protecting groups hereinbefore or hereinafter for P$^1$ taken together with P$^2$, or P$^4$ taken together with P$^5$, or P$^5$ taken together with P$^6$, to form a 1,3-dihydroxy protecting group, include those described in EPA 0319845 and GB 2244705, which are included herein by reference. Particularly suitable 1,3-dihydroxy protecting groups include, for example, the groups (a), (b), (c) and (d) illustrated below

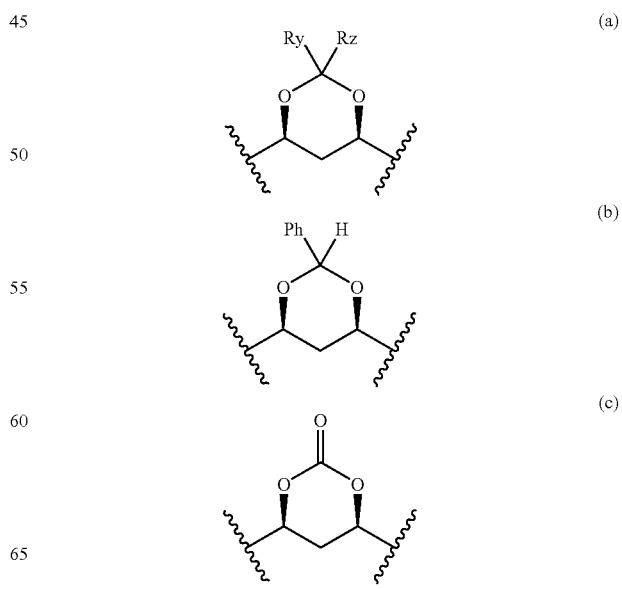

-continued

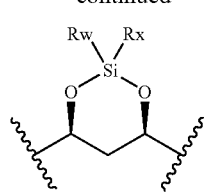

(d)

wherein Rw and Rx are independently (1-4C)alkyl, and Ry and Rz are independently (1-4C)alkyl, or one of Ry and Rz is (1-4C)alkyl and the other is hydrogen, or Ry and Rz taken together with the carbon atom to which they are attached form a cyclopentyl, cyclohexyl or cycloheptyl ring, and more particularly group (a) in which Ry and Rz are both methyl (i.e. an acetonide protecting group). Analogous protecting groups may also be used when $P^{11}$ together with $R^4$ forms a 1,3-dihydroxy protecting group.

Particularly suitable values for $R^1$, $R^2$, $R^3$ and $R^4$ include, for example, (1-4C)alkyl, such as methyl, ethyl, propyl, isopropyl, butyl and tert-butyl, especially the latter.

It will be appreciated that where more than one protecting group is removed after reacting a compound of the formula II with a compound of formula III, the protecting groups may be removed in any order which allows the compound of formula I to be obtained. It will also be appreciated that protecting groups and conditions for their removal may be chosen which allow for simultaneous removal of more than one protecting group. However it is preferred to carry out a final step under non-acidic conditions to avoid lactonisation of the compound of formula I.

A suitable pharmaceutically acceptable salt includes, for example, an alkali metal salt, for example a sodium or potassium salt, an alkaline earth metal salt, for example, calcium or magnesium salt, an ammonium salt or a salt with an organic base which affords a physiologically-acceptable cation, for example with methylamine, ethylamine, dimethylamine, trimethylamine, morpholine, diethanolamine, tris(2-hydroxyethyl)amine and tris(hydroxymethyl)methylamine.

When A is a group (ii), the asymmetric reduction of the carbonyl group adjacent to the carbon-carbon double bond may be carried out, for example, using diethylmethoxyborane and sodium borohydride. The reaction may be carried out, for example, in an alcohol-organic solvent mixture. The alcohol may be selected from, for example, methanol, ethanol, propanol and butanol. The non-alcoholic organic solvent may be selected from, for example, acetonitrile, diethyl ether, tetrahydrofuran and dimethylformamide. A particularly suitable combination of solvents is, for example, methanol and tetrahydrofuran. The reaction is generally carried out at a temperature between −100° C. to 20° C., for example between −85° C. to −70° C., under cooling for 10 minutes to 20 hours, for example 30 minutes to 10 hours.

When A is a group (iv), the asymmetric hydration of the carbon-carbon double bond may be carried out, for example, using benzyl aldehyde in the presence of a base, such as potassium tert-butoxide or potassium hexamethyldisilazide, in a suitable solvent, such as tetrahydrofuran, and at a temperature in the range of −20° C. to +10° C., such as about 0° C., by analogy with the procedure described in J. Org. Chem., 1993, 58, 2446-2453 which is hereby incorporated herein by reference.

When A is a group (vi), the asymmetric hydration of the carbon-carbon double bond may be carried out, for example, using an appropriate alcohol, such as allyl alcohol, in the presence of a base, such as LiOH, or benzyl alcohol in the presence of a base, such as NaOH, followed by reduction using palladium on carbon or palladium hydroxide on carbon under acidic conditions, by analogy with the procedure described in WO 02/05519, which is hereby incorporated herein by reference.

When A is a group (vii), the asymmetric reduction of the carbon-carbon double bond adjacent to the group $COOR^4$ may be carried out, for example, using similar conditions to those described above for the asymmetric reduction of the carbonyl group of A(ii).

Particular values of variable radicals or groups are as follows. Such values may be used where appropriate with any other of the values, definitions, claims or embodiments defined hereinbefore or hereinafter.

(1) in formula III, A is a group (i) wherein $P^1$ and $P^2$ together form an acetonide protecting group;

(2) in formula III, A is a group (i) wherein $P^1$ and $P^2$ are both hydrogen;

(3) in formula III, A is a group (ii) wherein $P^3$ is a hydroxy protecting group (4) in formula III, A is a group (ii) wherein $P^3$ is hydrogen (5) in formula III, A is a group (iii) wherein $P^4$ to $P^7$ are all hydroxy protecting groups (6) in formula III, A is a group (iii) wherein $P^4$ and $P^5$ are both hydrogen and $P^6$ and $P^7$ are the same or different hydroxy protecting groups (such as (1-4C)alkyl groups, for example methyl or ethyl)

(7) in formula III, A is a group (iv) wherein $P^8$ is a hydroxy protecting group (for example, trimethylsilyl (TMS), triethylsilyl (TES), tert-butyldiphenylsilyl (TBDPS) or tert-butyldimethylsilyl (TBDMS))

(8) in formula III, A is a group (iv) wherein $P^8$ is hydrogen (9) in formula III, A is a group (v) wherein $P^9$ is a hydroxy protecting group

(10) in formula III, A is a group (v) wherein $P^9$ is hydrogen

(11) in formula III, A is a group (vi)

(12) in formula III, A is a group (vii) wherein $P_{10}$ is hydrogen and $P^{11}$ together with $R^4$ is a 1,3-dihydroxy protecting group (for example, $P^{11}$ together with $R^4$ is an acetonide protecting group).

Starting materials of the formula II may be obtained, and conversion of a group Y into a group Z may be carried out, for example, as illustrated in the examples or as shown in Schemes 1 to 5 below, or by analogy therewith. It will be appreciated that when a compound of the formula II, wherein X is a group Y, is reacted with a compound of the formula III, then the intermediate obtained will include, for example, a compound as set out in Schemes 1 to 5 bearing the group -L, but in which the group -L is replaced by —CH═CH-A. The group Y may then be converted to the group $CH_3SO_2N$ ($CH_3$)— using one or more of the synthetic chemical steps illustrated in Schemes 1 to 5. In Schemes 1 to 5 and elsewhere herein, the following abbreviations are used:

EtOH=ethanol; NBS=N-bromosuccinimide; DMF=N,N-dimethylformamide; TEA=triethylamine; MeCN=acetonitrile; MsCl=mesyl chloride; TsCl=tosyl chloride; OTs=tosyloxy; THF=tetrahydrofuran; IPA=isopropanol; DCM=dichloromethane Scheme 1
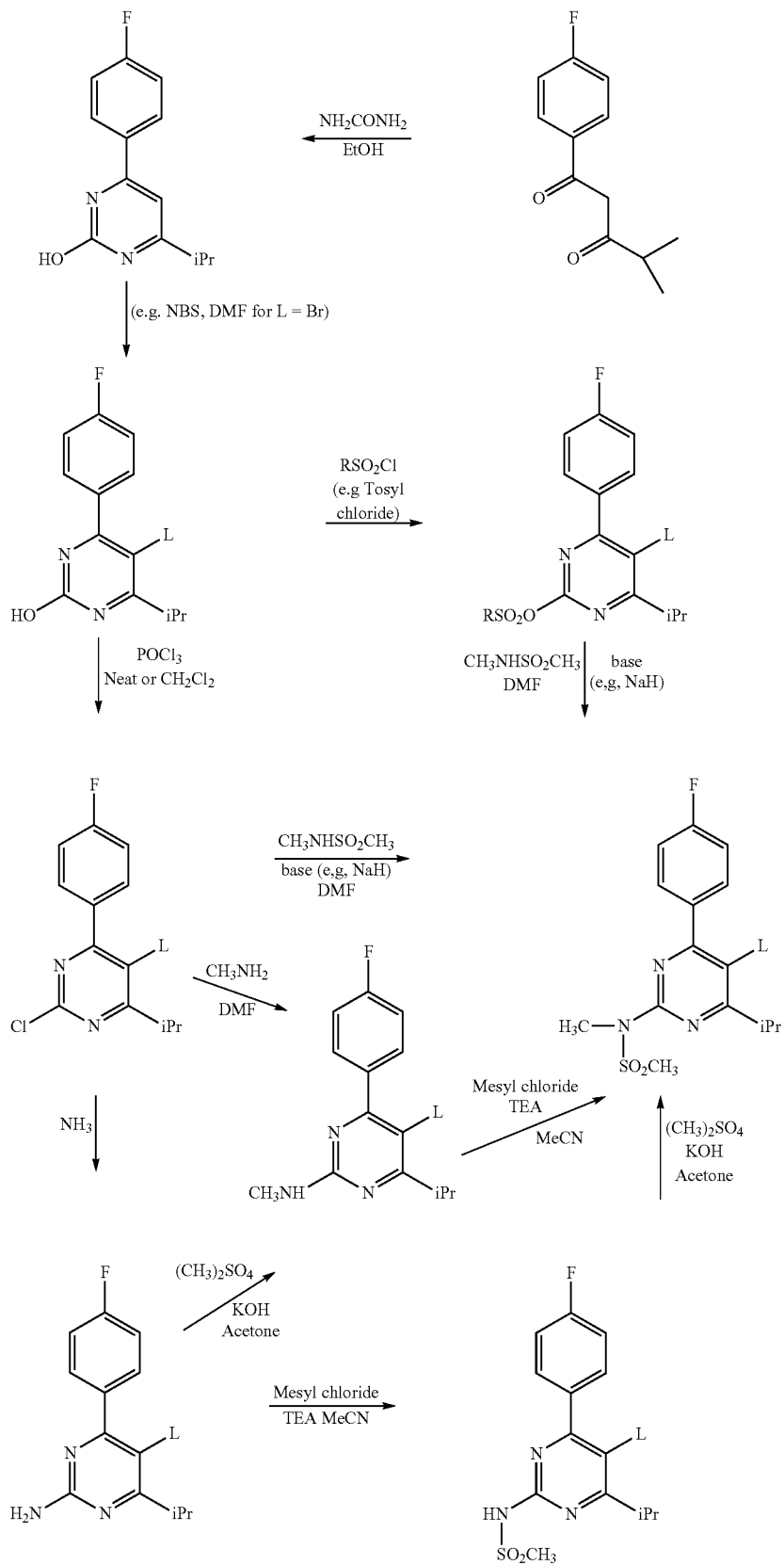

Scheme 2
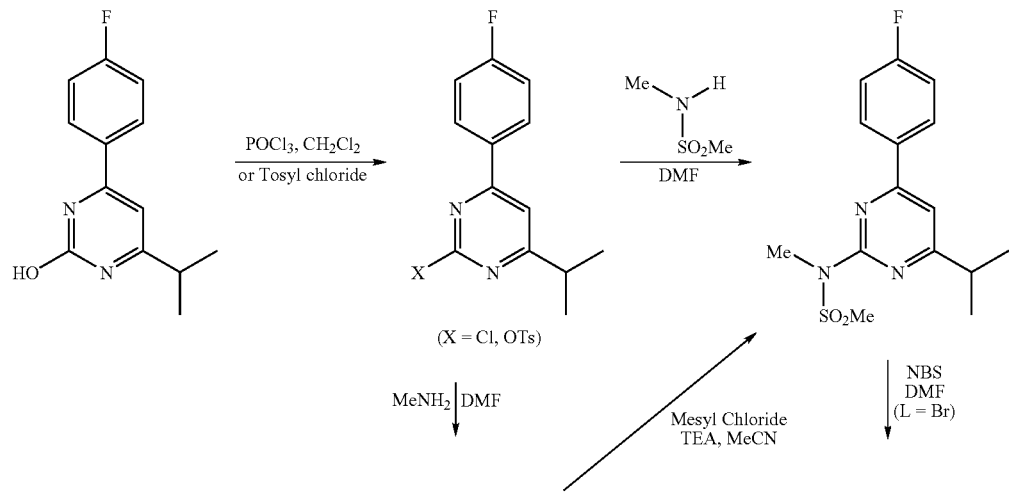
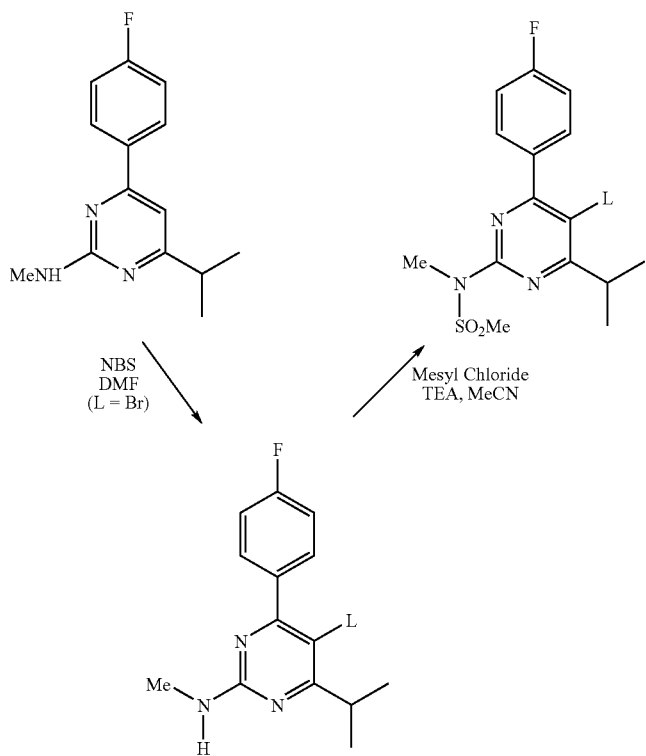

Scheme 3
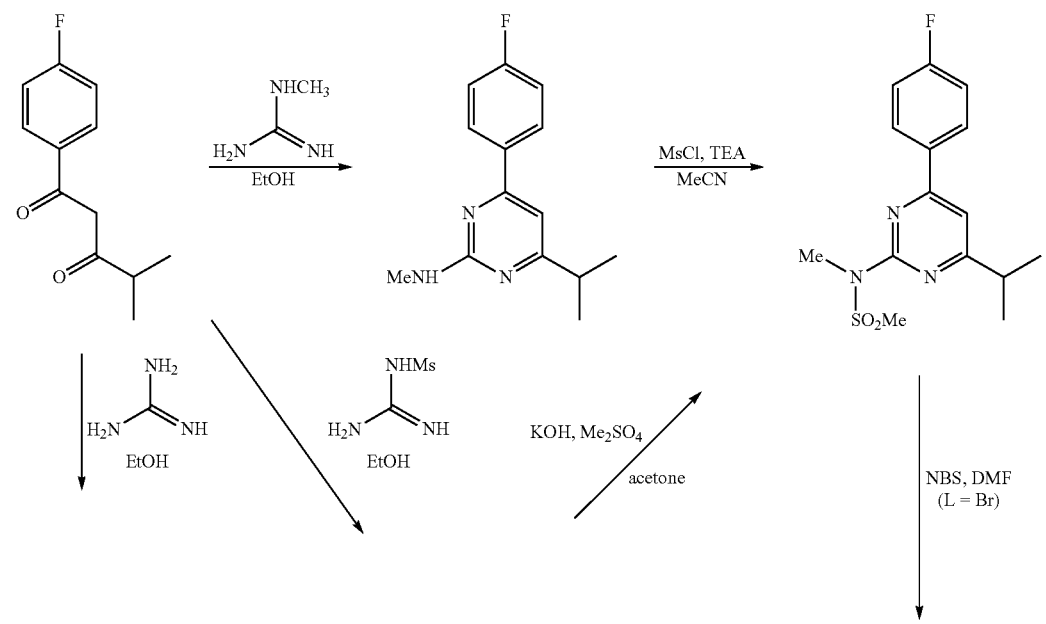
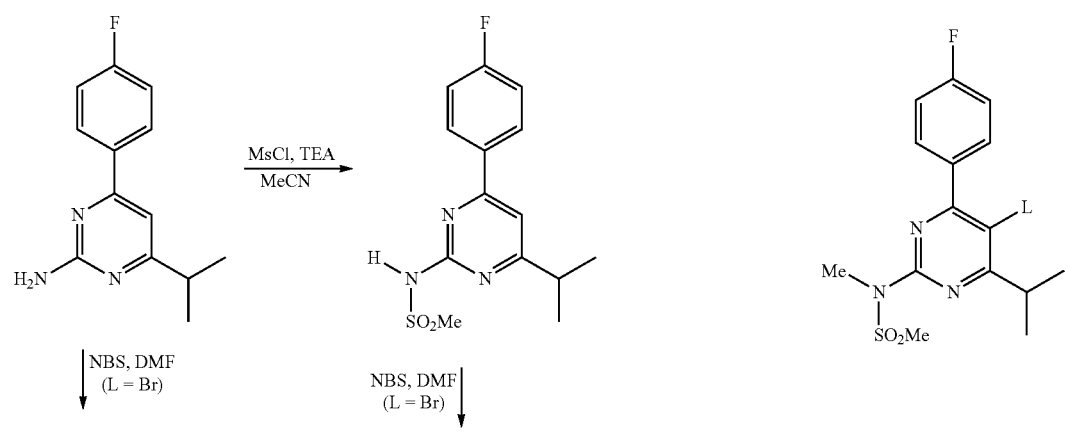
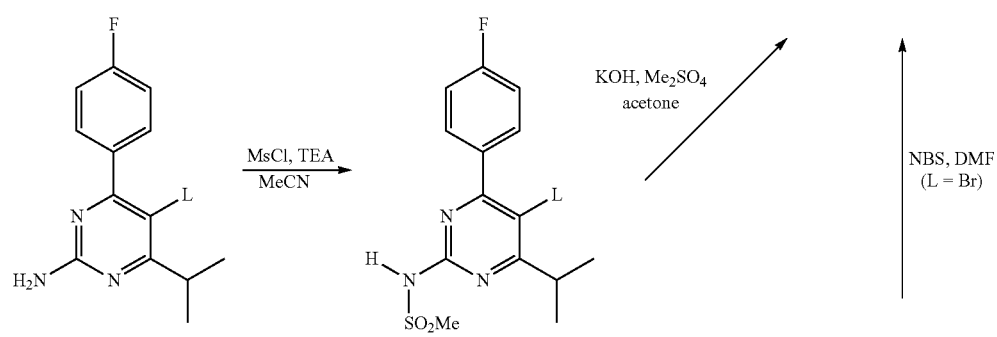

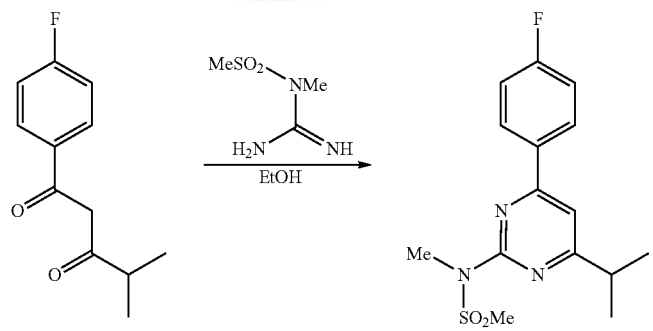
Scheme 4
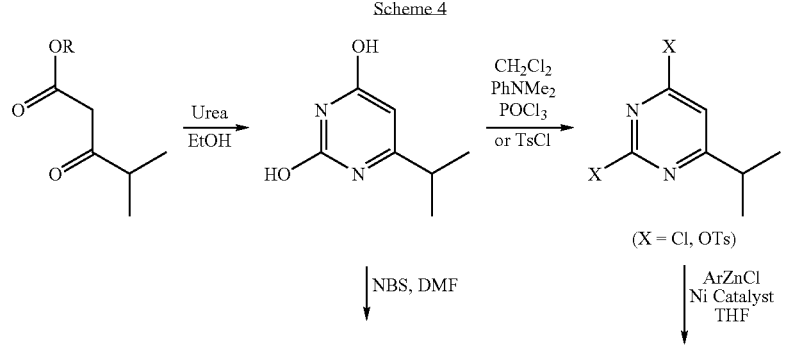
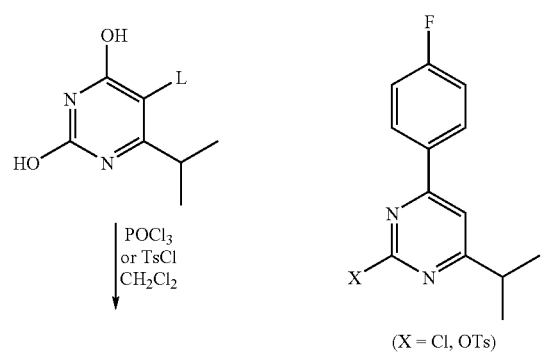
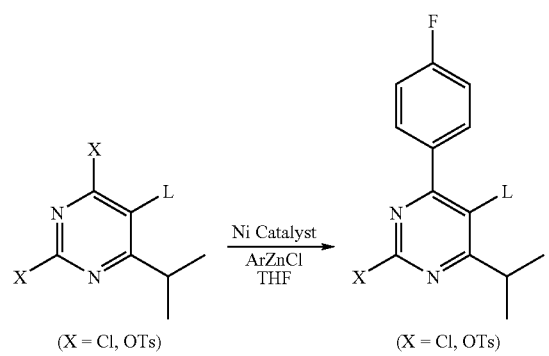

Scheme 5
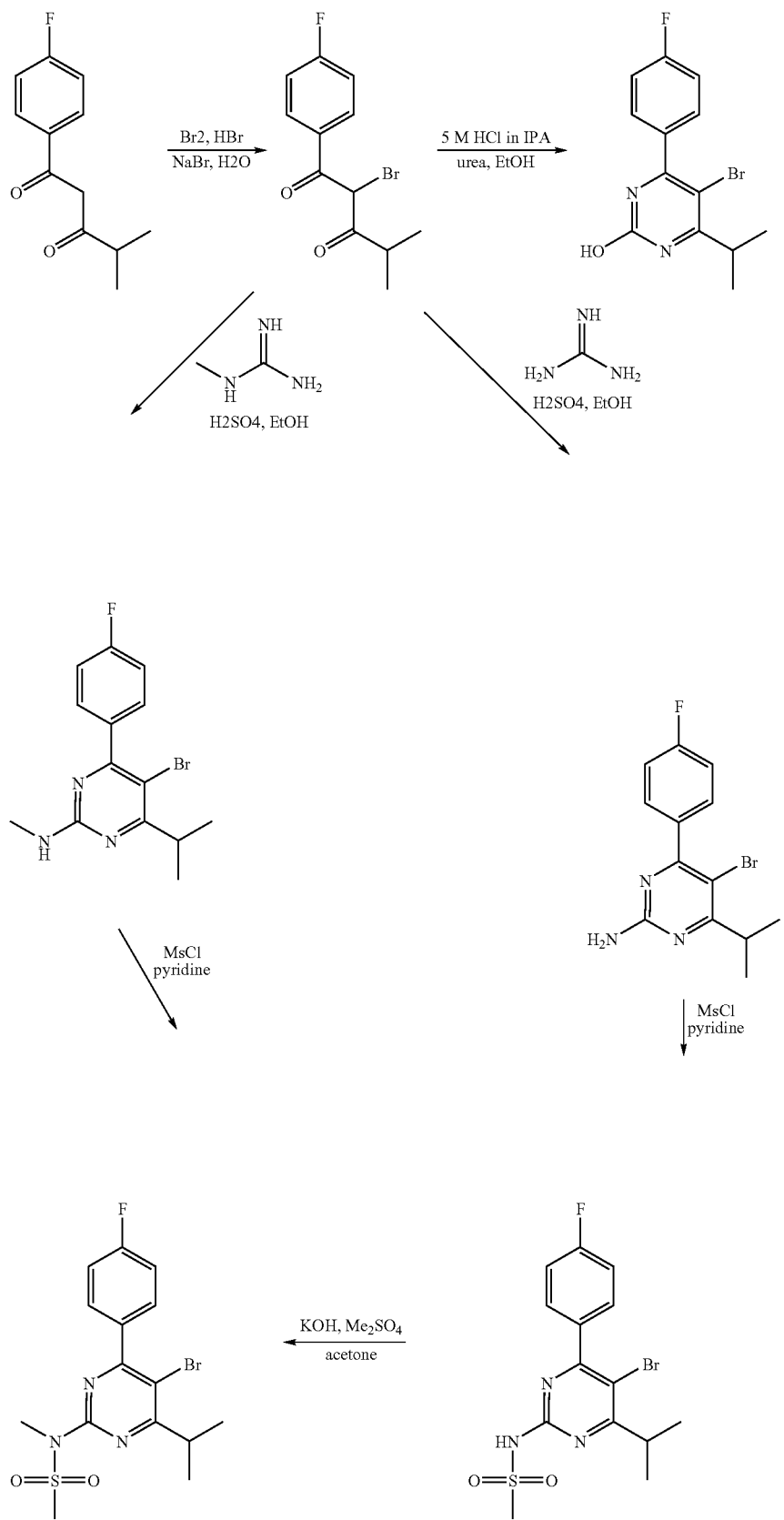

Starting materials of formula III are already known or may be obtained, for example, using analogous processes to those used for obtaining the known compounds or structurally related compounds or as illustrated in the examples hereinafter, or by analogy therewith.

A compound of the formula III wherein A is a group (i) may be obtained, for example, as described in Org. Lett., 2003, Vol. 5, No. 23, 4385-4388 or SynLett, 2003, page 215-218, or Tetrahedron Letters, 2002, 43(10), 1851-1854, or by analogy therewith.

A compound of the formula III wherein A is a group (ii) may be obtained, for example, as disclosed in WO 03/04450 or by analogy therewith, or by analogy with the procedure described in JACS, 2000, page 8837, as follows:

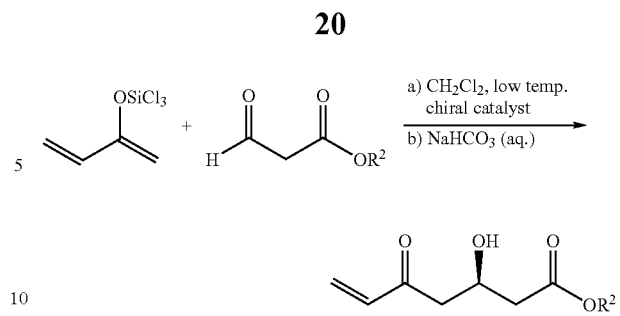

or by reduction of the corresponding tricarbonyl compound, by analogy with the disclosures in J. Org. Chem. 1991, p. 5752; Eur. J. Org. Chem. 1999, p. 3421 and PCT. Int. Appl., 2001004336, as follows:

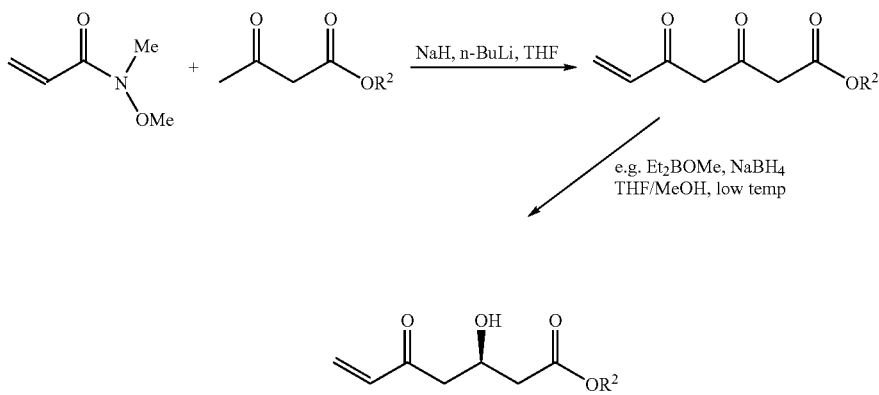

A compound of the formula III wherein A is a group (iii) may be obtained, for example, as follows:

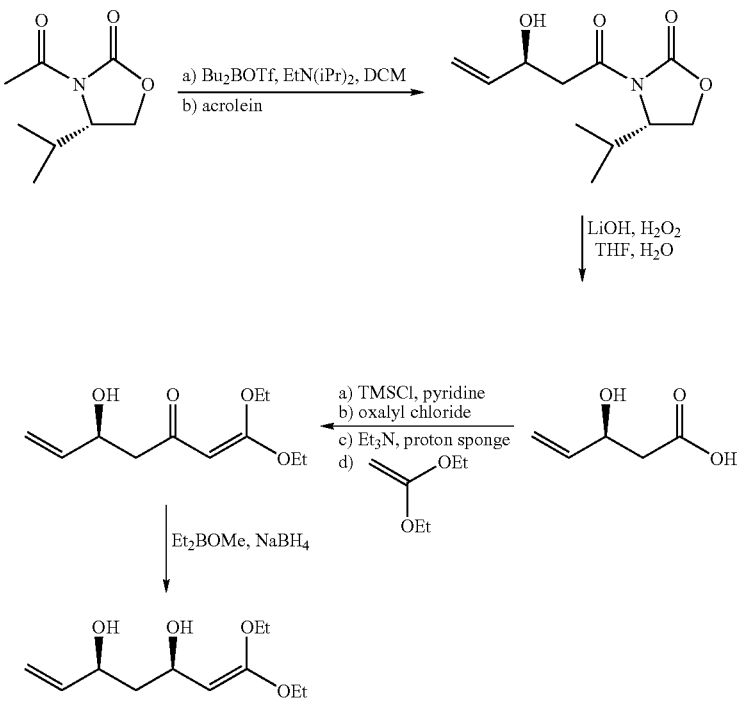

A compound of the formula III wherein A is a group (iv) may be obtained, for example, as disclosed in Org. Lett., 2004, Vol. 6, No. 20, 3465-3467, or as follows:

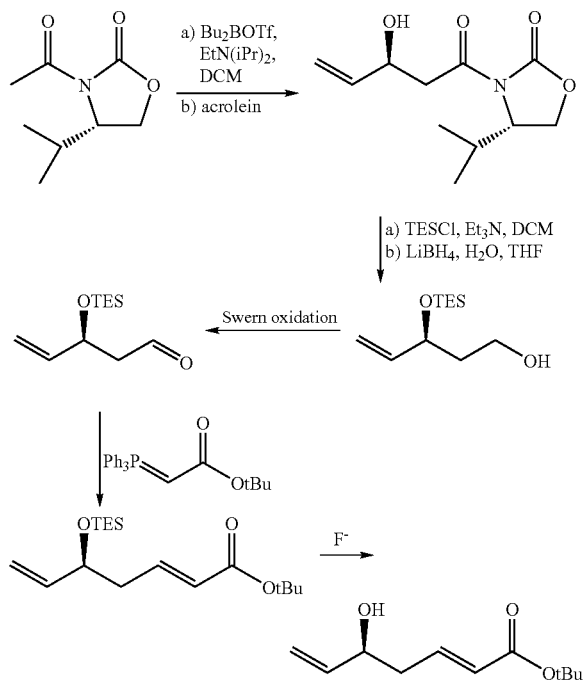

A compound of the formula III wherein A is a group (v) may be obtained as described in SynLett, 2003, page 215-218.

A compound of the formula III wherein A is a group (vi) may be obtained by analogy with the procedure described in Tetrahedron Lett., 2003, page 8081.

A compound of the formula III wherein A is a group (vii) may be obtained, for example, as described in Synlett 1999, No. 9, 1435-1437, or by analogy therewith.

A further aspect of the present invention comprises the manufacture of a compound of the formula I or a pharmaceutically acceptable salt thereof comprising reaction of a compound of the formula II wherein X is N-(methyl)methylsulfonylamino and L is a leaving group, with a compound of the formula III wherein A is a group (i) as set out hereinbefore wherein $P^1$ and $P^2$ are independently selected from hydrogen or a hydroxy-protecting group, or $P^1$ together with $P^2$ form a 1,3-dihydroxy protecting group (and particularly wherein $P^1$ and $P^2$ form together a 1,3-dihydroxy protecting group, and especially wherein $P^1$ and $P^2$ complete a group (a) defined herein wherein Ry and Rz are both methyl, i.e. an acetonide protecting group) and $R^1$ is a carboxy protecting group (such as (1-4C)alkyl and particularly tert-butyl), in the presence of a catalytically effective amount of a palladium catalyst and in the presence of a base as described above; whereafter the protecting groups $P^1$, $P^2$ and $R^1$ are removed in any order; whereafter when the product is obtained as the free acid, optionally forming a pharmaceutically acceptable salt of the compound of formula I, or when the product is obtained as a pharmaceutically acceptable salt, optionally converting the product to a different pharmaceutically acceptable salt. A further embodiment of this process comprises wherein a compound of the formula II is used in which X is N-(methyl) methylsulfonylamino and L is bromo. A further embodiment comprises wherein the latter compound is obtained from 5-bromo-2-hydroxy-4-(4-fluorophenyl)-6-isopropylpyrimidine, for example, by tosylation (such as by reaction with tosyl chloride) or chlorination (such as by reaction with phosphorus oxychloride), followed by reaction with N-methylmethanesulfonamide under basic conditions (for example in the presence of sodium hydride)). A further embodiment comprises wherein the 5-bromo-2-hydroxy-4-(4-fluorophenyl)-6-isopropylpyrimidine is obtained from 2-hydroxy-4-(4-fluorophenyl)-6-isopropylpyrimidine (for example by bromination with N-bromosuccinimide in DMF). A further embodiment comprises wherein the 2-hydroxy-4-(4-fluorophenyl)-6-isopropylpyrimidine is obtained from 1-(4-fluorophenyl)-4-methylpentane-1,3-dione (for example by reaction with urea under acidic conditions). A further embodiment comprises wherein the latter compound is obtained from an (1-4C)alkyl 4-fluorobenzoate (for example by reaction with 3-methyl-2-butanone in the presence of a base, such as potassium tert-butoxide). A further embodiment comprises wherein the protecting groups $P^1$ and $P^2$ are removed prior to removal of $R^1$.

Conversion of a compound of formula I obtained in the free acid form into a pharmaceutically acceptable salt form may be carried out using any of the procedures well known in the art for the formation of salts from carboxylic acids. Conversion of a compound of the formula I obtained in a salt form may be converted into a different pharmaceutically acceptable salt using any of the procedures will known in the art for the interconversion of salts, for example, conversion of the sodium salt to the calcium salt by treatment with a water soluble calcium salt (such as calcium chloride or calcium acetate) under aqueous conditions (for example as disclosed in EP 521471, WO 00/49014, WO 04/52867 and WO 04/108691). It will be appreciated that the conversion of the free acid to a salt, or a salt to an alternative salt, may be carried out in situ, that is without prior isolation of the free acid or initial salt form, and may involve one or more conventional steps, for example as illustrated in the examples or in the references given above).

A further aspect of the present invention comprises a process for the manufacture of a compound of the formula IV

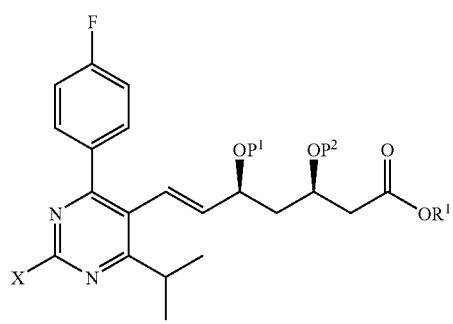

IV wherein $P^1$ and $P^2$ are independently hydroxy-protecting groups, or $P^1$ together with $P^2$ form a 1,3-dihydroxy protecting group, X is the group Z as defined above, and $R^1$ is a carboxy protecting group, comprising reaction of a compound of the formula II, wherein X is the group Z as defined above and L is a leaving group, with a compound of the formula III in which A is a group (i) as set out hereinbefore wherein $P^1$ and $P^2$ are independently hydroxy-protecting groups, or $P^1$ together with $P^2$ form a 1,3-dihydroxy protecting group (and particularly wherein $P^1$ and $P^2$ form together a 1,3-dihydroxy protecting group, and especially wherein $P^1$ and P² complete a group (a) defined herein wherein Ry and Rz are both methyl, i.e. an acetonide protecting group), and R¹ is a carboxy protecting group (such as (1-4C)alkyl and particularly tert-butyl), in the presence of a catalytically effective amount of a palladium catalyst and in the presence of a base as described above. Further embodiments of this process are wherein the starting material of formula II is obtained as described above.

A further aspect of the present invention comprises a process for the manufacture of a compound of the formula IV wherein P¹ and P² are independently hydroxy-protecting groups, or P¹ together with P² form a 1,3-dihydroxy protecting group, X is a group Y as defined above, and R¹ is a carboxy protecting group, comprising reaction of a compound of the formula II wherein X is a group Y as defined above and L is a leaving group, with a compound of the formula III wherein A is a group (i) as set out hereinbefore wherein P¹ and P² are independently hydroxy-protecting groups, or P¹ together with P² form a 1,3-dihydroxy protecting group (and particularly wherein P¹ and P² form together a 1,3-dihydroxy protecting group, and especially wherein P¹ and P² complete a group (a) defined herein wherein Ry and Rz are both methyl, i.e. an acetonide protecting group) and R¹ is a carboxy protecting group (such as (1-4C)alkyl and particularly tert-butyl), in the presence of a catalytically effective amount of a palladium catalyst and in the presence of a base as described above. Further separate independent embodiments of this process comprise the manufacture of compounds of the formula IV using a compound of the formula II wherein:
(i) X is hydroxy;
(ii) X is chloro;
(iii) X is amino;
(iv) X is methylamino;
(v) methanesulfonylamino; and
(vi) X is R$^x$SO$_2$O— wherein R$^x$ is (1-6C)alkyl (such as methyl, ethyl or propyl), aryl (such as phenyl) or substituted aryl (such as tolyl). The compounds of formula IV may be converted into a compound of formula I by removal of the protecting groups P¹, P² and R¹ as described herein. In a particular embodiment P¹ and P² are removed before R¹.

A further aspect of the present invention comprises a novel compound of the formula IV wherein X is a group Y as defined herein, P¹ and P² are independently hydroxy-protecting groups, or P¹ together with P² form a 1,3-dihydroxy protecting group, and R¹ is a carboxy protecting group. In particular a compound of the formula IV wherein X is hydroxy, chloro, bromo, iodo, amino, methylamino, benzylamino, N-benzylmethanesulfonylamino, R$^x$SO$_2$O— wherein R$^x$ is (1-6C)alkyl, aryl or substituted aryl, or R$^y$C(O)O— wherein R$^y$ is (1-6C)alkyl, aryl or substituted aryl, and P¹ together with P² are independently selected from hydrogen or a hydroxy-protecting group, or P¹ together with P² form a 1,3-dihydroxy protecting group and R¹ is (1-4C)alkyl.
Within this group of compounds, further particular independent groups of compounds are those in which (i) X is hydroxy; (ii) X is chloro; (iii) X is amino; (iv) X is methylamino; (v) X is R$^x$SO$_2$O— wherein R$^x$ is (1-6C)alkyl (such as methyl, ethyl or propyl), aryl (such as phenyl) or substituted aryl (such as tolyl). Particular compounds of formula IV include, for example, wherein
(1) X is hydroxy, P¹ and P² taken together form an acetonide (—C(CH$_3$)$_2$—) protecting group and R¹ is (1-4C)alkyl, especially tert-butyl;
(2) X is chloro, P¹ and P² taken together form an acetonide (—C(CH$_3$)$_2$—) protecting group and R¹ is (1-4C)alkyl, especially tert-butyl;
(3) X is amino, P¹ and P² taken together form an acetonide (—C(CH$_3$)$_2$—) protecting group and R¹ is (1-4C)alkyl, especially tert-butyl;
(4) X is methylamino, P¹ and P² taken together form an acetonide (—C(CH$_3$)$_2$—) protecting group and R¹ is (1-4C) alkyl, especially tert-butyl; and
(5) X is tosyloxy, P¹ and P² taken together form an acetonide (—C(CH$_3$)$_2$—) protecting group and R¹ is (1-4C)alkyl, especially tert-butyl A further aspect of the present invention comprises the manufacture of a compound of the formula V

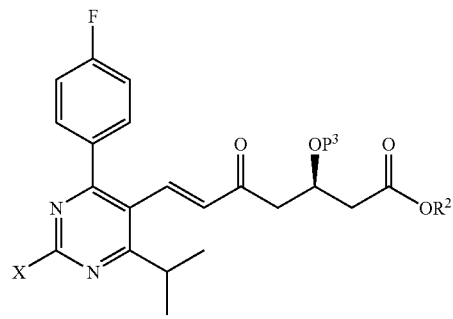

wherein P³ is hydrogen or a hydroxy-protecting group, X is the group Z as defined above, and R² is a carboxy protecting group comprising reaction of a compound of the formula II wherein X is the group Z and L is a leaving group with a compound of the formula III in which A is a group (ii) as set out hereinbefore wherein P³ is a hydrogen or a hydroxy-protecting group and R² is a carboxy protecting group, in the presence of a catalytically effective amount of a palladium catalyst and in the presence of a base as described above.

A further aspect of the present invention comprises the manufacture of a compound of the formula V wherein P³ is a hydroxy-protecting group, X is a group Y as defined above, and R² is a carboxy protecting group, comprising reaction of a compound of the formula II wherein X is the group Y as defined herein and L is a leaving group, with a compound of the formula III in which A is a group (ii) as set out hereinbefore wherein P³ is a hydroxy-protecting group and R² is a carboxy protecting group, in the presence of a catalytically effective amount of a palladium catalyst and in the presence of a base. Further separate independent embodiments of this process comprise the manufacture of compounds of the formula V using a compound of the formula II wherein:
(i) X is hydroxy;
(ii) X is chloro;
(iii) X is amino;
(iv) X is methylamino;
(v) methanesulfonylamino; and
(vi) X is R$^x$SO$_2$O— wherein R$^x$ is (1-6C)alkyl (such as methyl, ethyl or propyl), aryl (such as phenyl) or substituted aryl (such as tolyl). The compounds of formula V may be converted into a compound of formula I by converting the group Y into the group Z, followed by carrying out in any order the steps of (1) asymmetric reduction of the carbonyl group adjacent to the carbon-carbon double bond; (2) removal of P³; and removal of the carboxy protecting group R², as described herein. In a particular embodiment, the asymmetric reduction is carried out before removal of the protecting groups.

A further aspect of the present invention comprises novel compounds of the formula V.

A further aspect of the present invention comprises the manufacture of a compound of the formula VI

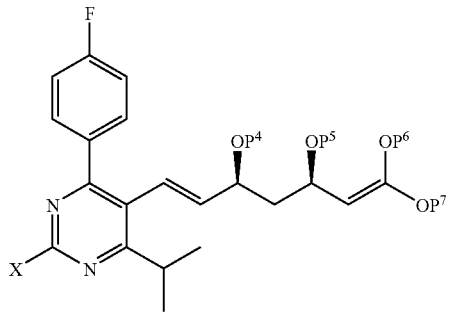

VI wherein $P^4$, $P^5$, $P^6$ and $P^7$ are independently hydroxy-protecting groups, or $P^4$ together with $P^5$ or $P^5$ together with $P^6$ form a 1,3-dihydroxy protecting group, and X is the group Z as defined herein, comprising reaction of a compound of the formula II as defined above, wherein X is the group Z as defined herein and L is a leaving group, with a compound of the formula III in which A is a group (iii) as set out hereinbefore wherein $P^4$, $P^5$, $P^6$ and $P^7$ are independently hydroxy-protecting groups, or $P^4$ together with $P^5$ or $P^5$ together with $P^6$ form a 1,3-dihydroxy protecting group, in the presence of a catalytically effective amount of a palladium catalyst and in the presence of a base as described above.

A further aspect of the present invention comprises the manufacture of a compound of the formula VI wherein $P^4$, $P^5$, $P^6$ and $P^7$ are independently hydroxy-protecting groups, or $P^4$ together with $P^5$ or $P^5$ together with $P^6$ form a 1,3-dihydroxy protecting group, and X is a group Y as defined herein, comprising reaction of a compound of the formula II, wherein X is a group Y as defined above and L is a leaving group, with a compound of the formula III in which A is a group (iii) as set out hereinbefore wherein $P^4$, $P^5$, $P^6$ and $P^7$ are independently hydroxy-protecting groups, or $P^4$ together with $P^5$ or $P^5$ together with $P^6$ form a 1,3-dihydroxy protecting group, in the presence of a catalytically effective amount of a palladium catalyst and in the presence of a base as described above. Further separate independent embodiments of this process comprise the manufacture of compounds of the formula VI using a compound of the formula II wherein:

(i) X is hydroxy;

(ii) X is chloro;

(iii) X is amino;

(iv) X is methylamino;

(v) methanesulfonylamino; and (vi) X is $R^xSO_2O$— wherein $R^x$ is (1-6C)alkyl (such as methyl, ethyl or propyl), aryl (such as phenyl) or substituted aryl (such as tolyl). The compounds of formula VI may be converted into a compound of formula I by converting the group Y into the group Z, followed by carrying out in any order the removal of $P^4$, $P^5$, $P^6$ and $P^7$, as described herein.

A further aspect of the present invention comprises novel compounds of the formula VI.

A further aspect of the present invention comprises the manufacture of a compound of the formula VII

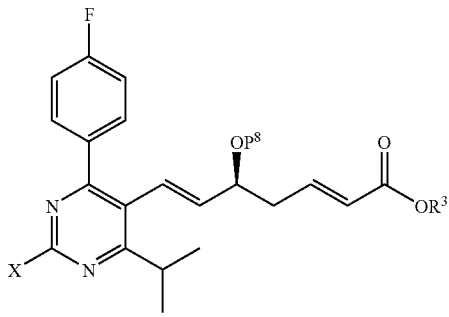

VII wherein $P^8$ is a hydroxy-protecting group, X is the group Z as defined above, and $R^3$ is a carboxy protecting group comprising reaction of a compound of the formula II wherein X is the group Z and L is a leaving group with a compound of the formula III in which A is a group (iv) as set out hereinbefore wherein $P^8$ is a hydroxy-protecting group and $R^3$ is a carboxy protecting group, in the presence of a catalytically effective amount of a palladium catalyst and in the presence of a base as described above.

A further aspect of the present invention comprises the manufacture of a compound of the formula VII wherein $P^8$ is a hydroxy-protecting group, X is a group Y as defined above, and $R^3$ is a carboxy protecting group comprising reaction of a compound of the formula II wherein X is a group Y and L is a leaving group with a compound of the formula III in which A is a group (iv) as set out hereinbefore wherein $P^8$ is a hydroxy-protecting group and $R^3$ is a carboxy protecting group, in the presence of a catalytically effective amount of a palladium catalyst and in the presence of a base. Further separate independent embodiments of this process comprise the manufacture of compounds of the formula VII using a compound of the formula II wherein:

(i) X is hydroxy;

(ii) X is chloro;

(iii) X is amino;

(iv) X is methylamino;

(v) methanesulfonylamino; and (vi) X is $R^xSO_2O$— wherein $R^x$ is (1-6C)alkyl (such as methyl, ethyl or propyl), aryl (such as phenyl) or substituted aryl (such as tolyl). The compounds of formula VII may be converted into a compound of formula I by converting the group Y into the group Z, followed by carrying out in any order the steps of (1) removal of $P^8$; (2) asymmetric hydration of the carbon-carbon double bond adjacent to the ester group $COOR^3$; and (3) removal of $R^3$, as described herein. In a particular embodiment, the asymmetric hydration is carried out before $P^8$ and $R^3$ are removed.

A further aspect of the present invention comprises novel compounds of the formula VII.

A further aspect of the present invention comprises the manufacture of a compound of the formula VIII

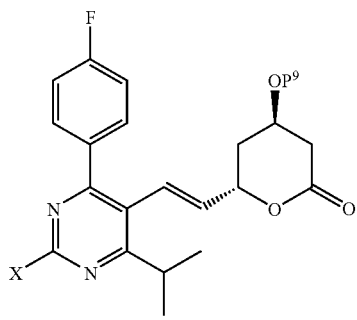

VIII wherein P⁹ is hydrogen or a hydroxy-protecting group and X is the group Z as defined above, comprising reaction of a compound of the formula II wherein X is the group Z and L is a leaving group with a compound of the formula III in which A is a group (v) as set out hereinbefore wherein P⁹ is a hydroxy-protecting group, in the presence of a catalytically effective amount of a palladium catalyst and in the presence of a base as described above.

A further aspect of the present invention comprises the manufacture of a compound of the formula VIII wherein P⁹ is hydrogen or a hydroxy-protecting group and X is a group Y as defined above, comprising reaction of a compound of the formula II wherein X is a group Y and L is a leaving group with a compound of the formula III in which A is a group (v) as set out hereinbefore wherein P⁹ is a hydroxy-protecting group, in the presence of a catalytically effective amount of a palladium catalyst and in the presence of a base. Further separate independent embodiments of this process comprise the manufacture of compounds of the formula VIII using a compound of the formula II wherein:

(i) X is hydroxy;

(ii) X is chloro;

(iii) X is amino;

(iv) X is methylamino;

(v) methanesulfonylamino; and (vi) X is R$^x$SO$_2$O— wherein R$^x$ is (1-6C)alkyl (such as methyl, ethyl or propyl), aryl (such as phenyl) or substituted aryl (such as tolyl). The compounds of formula VIII may be converted into a compound of formula I by converting the group Y into the group Z, followed by carrying out in any order the steps of (1) removal of the protecting group P⁹ if present and (2) ring opening by hydrolysis under basic conditions, as described herein. In a particular embodiment, P⁹ is a hydroxy protecting group.

A further aspect of the present invention comprises novel compounds of the formula VIII.

A further aspect of the present invention comprises the manufacture of a compound of the formula IX

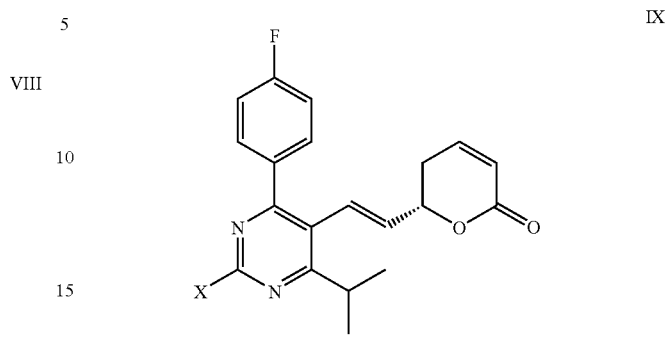

IX wherein X is the group Z as defined above, comprising reaction of a compound of the formula II wherein X is the group Z and L is a leaving group with a compound of the formula III in which A is a group (vi) as set out hereinbefore, in the presence of a catalytically effective amount of a palladium catalyst and in the presence of a base as described above.

A further aspect of the present invention comprises the manufacture of a compound of the formula IX wherein X is a group Y as defined above, comprising reaction of a compound of the formula II wherein X is a group Y and L is a leaving group with a compound of the formula III in which A is a group (vi) as set out hereinbefore, in the presence of a catalytically effective amount of a palladium catalyst and in the presence of a base. Further separate independent embodiments of this process comprise the manufacture of compounds of the formula IX using a compound of the formula II wherein:

(i) X is hydroxy;

(ii) X is chloro;

(iii) X is amino;

(iv) X is methylamino;

(v) methanesulfonylamino; and (vi) X is R$^x$SO$_2$O— wherein R$^x$ is (1-6C)alkyl (such as methyl, ethyl or propyl), aryl (such as phenyl) or substituted aryl (such as tolyl). The compounds of formula IX may be converted into a compound of formula I by converting the group Y into the group Z, followed by carrying out in any order the steps of as (1) asymmetric hydration of the ring carbon-carbon double bond and (2) hydrolysis under basic conditions, as described herein. In a particular embodiment, the asymmetric hydration is carried out prior to hydrolysis.

A further aspect of the present invention comprises novel compounds of the formula IX.

A further aspect of the present invention comprises the manufacture of a compound of the formula X

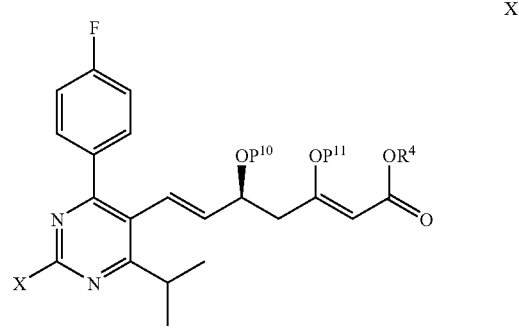

X wherein $P^{10}$ and $P^{11}$ are independently selected from hydrogen and a hydroxy protecting group, or $P^{10}$ together with $P^{11}$, or $P^{11}$ together with $R^4$, form a 1,3-dihydroxy protecting group; X is the group Z as defined herein; and $R^4$ is a carboxy protecting group comprising reaction of a compound of the formula II as defined above, wherein X is the group Z as defined herein and L is a leaving group, with a compound of the formula III in which A is a group (vii) as set out hereinbefore wherein $P^{10}$ and $P^{11}$ are independently selected from hydrogen and a hydroxy protecting group, or $P_{10}$ together with $P^{11}$ form a 1,3-dihydroxy protecting group, in the presence of a catalytically effective amount of a palladium catalyst and in the presence of a base as described above.

A further aspect of the present invention comprises the manufacture of a compound of the formula X wherein $P^{10}$ and $P^{11}$ are independently selected from hydrogen and a hydroxy protecting group, or $P^{10}$ together with $P^{11}$, or $P^{11}$ together with $R^4$, form a 1,3-dihydroxy protecting group; X is the group Y as defined herein; and $R^4$ is a carboxy protecting group, comprising reaction of a compound of the formula II, wherein X is a group Y as defined above and L is a leaving group, with a compound of the formula III in which A is a group (vii) as set out hereinbefore wherein $P^{10}$ and $P^{11}$ are independently selected from hydrogen and a hydroxy protecting group, or $P_{10}$ together with $P^{11}$, or $P^{11}$ together with $R^4$, form a 1,3-dihydroxy protecting group, in the presence of a catalytically effective amount of a palladium catalyst and in the presence of a base. Further separate independent embodiments of this process comprise the manufacture of compounds of the formula X using a compound of the formula II wherein:
(i) X is hydroxy;
(ii) X is chloro;
(iii) X is amino;
(iv) X is methylamino;
(v) methanesulfonylamino; and
(vi) X is $R^xSO_2O$— wherein $R^x$ is (1-6C)alkyl (such as methyl, ethyl or propyl), aryl (such as phenyl) or substituted aryl (such as tolyl). The compounds of formula X may be converted into a compound of formula I by converting the group Y into the group Z, followed by carrying out in any order the steps of (1) asymmetric reduction of the carbon-carbon adjacent to the group $COOR^4$; (2) removal of the protecting groups, as described herein. In a particular embodiment, $P^{11}$ is hydrogen.

A further aspect of the present invention comprises novel compounds of the formula X.

Further independent embodiments of the invention comprise any of the processes described above wherein the starting material of formula II is obtained from a compound of the formula XI.

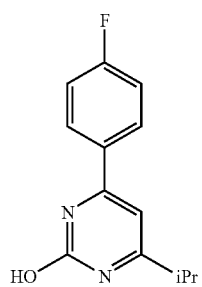

by carrying out one or more chemical reactions, for example, as shown in any of Schemes 1 to 5, or as illustrated in the Examples hereinafter. In particular where the compound of formula II is 5-bromo-2-hydroxy-4-(4-fluorophenyl)-6-isopropylpyrimidine and is obtained from 2-hydroxy-4-(4-fluorophenyl)-6-isopropylpyrimidine (formula XI) by bromination, for example with N-bromosuccinimide in DMF.

A further aspect of the present invention comprises novel compounds of the formula II. Particular novel compounds of formula II include, for example,
5-bromo-4-(4-fluorophenyl)-6-isopropyl-2-(N-methyl-N-methylsulfonylamino)pyrimidine;
5-iodo-4-(4-fluorophenyl)-6-isopropyl-2-(N-methyl-N-methylsulfonylamino)pyrimidine;
5-chloro-4-(4-fluorophenyl)-6-isopropyl-2-(N-methyl-N-methylsulfonylamino)pyrimidine;
5-trifluoromethylsulfonyloxy-4-(4-fluorophenyl)-6-isopropyl-2-(N-methyl-N-methylsulfonylamino)pyrimidine;
5-bromo-4-(4-fluorophenyl)-6-isopropyl-2-hydroxypyrimidine;
5-iodo-4-(4-fluorophenyl)-6-isopropyl-2-hydroxypyrimidine;
5-chloro-4-(4-fluorophenyl)-6-isopropyl-2-hydroxypyrimidine;
5-trifluoromethylsulfonyloxy-4-(4-fluorophenyl)-6-isopropyl-2-hydroxypyrimidine;
5-bromo-4-(4-fluorophenyl)-6-isopropyl-2-chloropyrimidine;
5-iodo-4-(4-fluorophenyl)-6-isopropyl-2-chloropyrimidine;
5-chloro-4-(4-fluorophenyl)-6-isopropyl-2-chloropyrimidine;
5-trifluoromethylsulfonyloxy-4-(4-fluorophenyl)-6-isopropyl-2-chloropyrimidine;
5-bromo-4-(4-fluorophenyl)-6-isopropyl-2-tosyloxypyrimidine;
5-iodo-4-(4-fluorophenyl)-6-isopropyl-2-tosyloxypyrimidine;
5-chloro-4-(4-fluorophenyl)-6-isopropyl-2-tosyloxypyrimidine;
5-trifluoromethylsulfonyloxy-4-(4-fluorophenyl)-6-isopropyl-2-tosyloxypyrimidine;
5-bromo-4-(4-fluorophenyl)-6-isopropyl-2-methylaminopyrimidine;
5-iodo-4-(4-fluorophenyl)-6-isopropyl-2-methylaminopyrimidine;
5-chloro-4-(4-fluorophenyl)-6-isopropyl-2-methylaminopyrimidine;
5-trifluoromethylsulfonyloxy-4-(4-fluorophenyl)-6-isopropyl-2-methylaminopyrimidine;
5-bromo-4-(4-fluorophenyl)-6-isopropyl-2-methanesulfonylaminopyrimidine;
5-iodo-4-(4-fluorophenyl)-6-isopropyl-2-methanesulfonylaminopyrimidine;
5-chloro-4-(4-fluorophenyl)-6-isopropyl-2-methanesulfonylaminopyrimidine;
5-trifluoromethylsulfonyloxy-4-(4-fluorophenyl)-6-isopropyl-2-methanesulfonylaminopyrimidine;
5-bromo-4-(4-fluorophenyl)-6-isopropyl-2-aminopyrimidine;
5-iodo-4-(4-fluorophenyl)-6-isopropyl-2-aminopyrimidine;
5-chloro-4-(4-fluorophenyl)-6-isopropyl-2-aminopyrimidine; and
5-trifluoromethylsulfonyloxy-4-(4-fluorophenyl)-6-isopropyl-2-aminopyrimidine; and the salts thereof.

A further aspect of the present invention comprises novel starting materials for obtaining compounds of the formula II including, for example, 2-hydroxy-4-(4-fluorophenyl)-6-isopropylpyrimidine (formula XI).

A still further aspect of the invention comprises a process for the production of 2-hydroxy-4-(4-fluorophenyl)-6-isopropylpyrimidine said process comprising a) reaction of ethyl-4-fluorobenzoate with 3-methyl-2-butanone in toluene to give 1-(4-fluorophenyl)-4-methylpentane-1,3-dione as a solution in toluene; and b) reaction of said solution in toluene with urea and hydrogen chloride in isopropanol.

Advantageously, the above process, which starts from simple starting materials, efficiently avoids the need to isolate the intermediate 1-(4-fluorophenyl)-4-methylpentane-1,3-dione because toluene is present as a solvent in both steps. The second step is generally carried out at elevated temperatures, for example at about 80°. Suitable conditions for carrying out this process are as illustrated in the accompanying examples.

The invention is further illustrated, but not limited by, the following Examples.

EXAMPLE 1

A mixture of N-(5-bromo-4-(4-fluorophenyl)-6-isopropylpyrimidin-2-yl)-N-methylmethanesulfonamide (1.00 g, 2.50 mmol), bis-tri-tert-butylphosphine palladium (0) (131 mg, 0.250 mmol), tert-butyl 2-((4R,6S)-2,2-dimethyl-6-vinyl-1,3-dioxan-4-yl)acetate (640 mg, 2.50 mmol), water (5 mL), N,N-dicyclohexylmethylamine (0.530 mL, 2.50 mmol), and N,N-dimethylformamide (5 mL) was heated and stirred at 50° C. under nitrogen for four days. The mixture was then diluted with ethyl acetate (11 mL), water (10 mL), and acetic acid (0.2 mL). The organic phase was separated and the aqueous phase was extracted with ethyl acetate (5 mL). The combined organic phases were washed with water (10 mL), then brine (10 mL), and concentrated in vacuo to give a yellow oil containing some solids. This material was adsorbed onto silica gel through dissolution in ethyl acetate, then purified by flash chromatography (5% ethyl acetate in isohexane gradually increasing to 20% ethyl acetate in hexane, silica column 25 mm in diameter and 250 mm in height) to yield tert-butyl 2-((4R,6S)-6-((E)-2-(4-(4-fluorophenyl)-6-isopropyl-2-(N-methylmethanesulfonamido)pyrimidin-5-yl)vinyl)-2,2-dimethyl-1,3-dioxan-4-yl)acetate of the formula

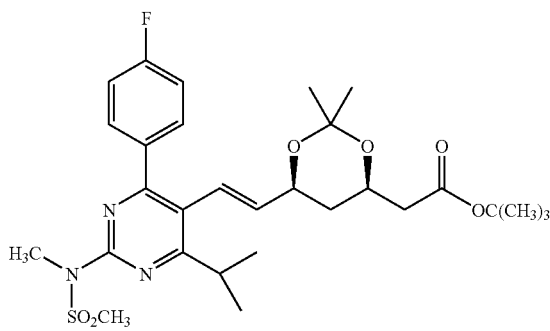

(hereinafter referred to as BEM) as a white solid (204 mg). The isolated product was spectroscopically identical to the compound BEM described in International Patent Application, Publication No. WO 00/49014.

The compound BEM can then be converted into rosuvastatin calcium as described in International Patent Application, Publication No. WO 00/49014 (incorporated herein in full by reference) as follows:—

A mixture of BEM (5.0 g) and acetonitrile (35 ml) was stirred under an inert atmosphere at 40° C. 0.02M hydrochloric acid (9.5 ml) was added over 30 minutes to the resultant solution, maintaining the temperature at 35° C. to 42° C. The mixture was stirred at 40° C. for 3 hours then cooled to 25° C. 1.0M sodium hydroxide solution (9.5 ml) was added with stirring at 25° C. and the mixture was stirred for an additional one hour at 25° C. Sodium chloride (4.7 g) was added and the mixture was cooled to −5° C. over one hour. Sufficient of a solution of 1M hydrochloric acid (9.5 ml) and sodium chloride (2.4 g) was added at −5° C. to achieve a pH of 3.4 to 4.0 and the mixture stirred at this temperature for 5 minutes. The mixture was allowed to settle for 10 minutes at −5° C. to give two layers. The lower layer was separated and discarded. Acetonitrile (65 ml) at −5° C. was added to the remaining solution and the mixture was filtered through a filter agent. 40% methylamine solution in water (1.1 ml) was added at −5° C. and the mixture was warmed to 30° C. over 40 minutes and maintained at this temperature for 90 minutes. The mixture was then cooled to 0° C. over 40 minutes and maintained at this temperature for 90 minutes. The resultant solid was collected by filtration and washed with acetonitrile (2×12 ml). The solid, which is the methylamine salt of the compound of formula IV ($R^1$=MeNH$_3^+$), was dried under vacuum at 35° C. (3.87 g). 8% w/w aqueous sodium hydroxide (5.44 ml) was added to a stirred mixture of the methylamine salt (6.0 g) in degassed water (30 ml) at 20° C. and the mixture was stirred for one hour. The mixture was filtered and concentrated under reduced pressure at 40° C. until 24 ml of distillate collected. Water (24 ml) was added and the mixture again concentrated under reduced pressure at 40° C. until 24 ml of distillate collected. Water (30 ml) was added and a solution of calcium chloride dihydrate (1.03 g) in water (6 ml) was added dropwise at 20° C. The mixture was stirred for 45 minutes and the resultant solid filtered. The solid was washed with water (36 ml) and dried under vacuum at 40° C. to give the calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid.

Alternatively the compound BEM may be converted into rosuvastatin calcium as described in International Patent Application WO 04/108691 (incorporated herein in full by reference) as follows: BEM (20.0 g) was dissolved in acetonitrile (140 ml) at 40° C., then cooled to 35° C. before gradual addition of hydrochloric acid (0.02M, 35 ml) at 35° C. The resulting solution was stirred at 35° C. until the reaction was complete then cooled to 25° C. Sodium hydroxide (1.0M, 38 ml) was added at 25° C. and the resulting mixture stirred at this temperature until the reaction was complete. Aqueous hydrochloric acid (1M) was added to adjust the pH of the solution to pH9. The solution was distilled under reduced pressure (52 mBar, ≦40° C.) until approximately 100 ml of acetonitrile/water had been removed. Water (100 ml) was added and distillation continued until a further 100 ml of acetonitrile/water had been removed. The resulting mixture was filtered through a filter pad, the filter washed with water (30 ml) and the filtrates heated to 40° C. before addition of a solution of calcium chloride dihydrate (3.07 g) in water (29.5 ml) over 20 min, maintaining the reaction mixture at 38-41° C.

The reaction mixture was stirred for a further 15 min at 40° C., then cooled to 20° C. and stirred at this temperature for a further 15 min. The resulting suspension was filtered, washed with water (3×50 ml) and dried to give (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt (15.8 g, 84% yield);
and as follows:

BEM (20.0 g) was dissolved in acetonitrile (140 ml) at 40° C., then cooled to 35° C. before gradual addition of hydrochloric acid (0.02M, 35 ml) at 35° C. The resulting solution was stirred at 35° C. until the reaction was complete then cooled to 25° C. Further acetonitrile (8 ml) was added before sodium hydroxide (1.0M, 38 ml) was added at 25° C. and the resulting mixture stirred at this temperature until the reaction was complete. Aqueous hydrochloric acid (0.1M) was added to adjust the pH of the solution to approximately pH10.5. Water was added so that the combined volume of water and hydrochloric acid (0.1M) (from the previous pH adjustment step) added was 100 ml. Toluene (125 ml) was then added and the mixture stirred at 40° C. for 30 minutes before it was allowed to settle for 1 hour at 40° C. The aqueous phase was then separated from the organic phase at 40° C. The aqueous phase was distilled under reduced pressure (53 mBar, ≦40° C.) until the volume was reduced to 135 ml. The resulting aqueous solution was filtered through a filter pad and the filter washed with water and combined with the aqueous reaction solution, such that the total volume of the resulting aqueous solution was 170 ml. This solution was heated to 40° C. before addition of a solution of calcium chloride di-hydrate (3.05 g) in water (29.5 ml) over 20 min, maintaining the reaction mixture at 38-41° C.

The reaction mixture was stirred for a further 15 min at 40° C., then cooled to 20° C. and stirred at this temperature for a further 15 min. The resulting suspension was filtered, washed with water (3×53 ml) and dried to give (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt (14.7 g@100% strength, 85% yield).

$^1$HNMR δ: 1.21 (d+d, 6H) 1.32 (dt, 1H) 1.51 (dt, 1H) 2.00 (dd, 1H) 2.14 (dd, 1H) 3.42 (spt, 1H)* 3.45 (s, 3H) 3.54 (s, 3H) 3.77 (m, 1H) 4.21 (q, 1H) 5.53 (dd, 1H) 6.51 (dd, 1H) 7.27 (t, 2H) 7.71 (dd, 2H)
*partially obscured
[The $^1$H NMR was carried out as a 3% w/v solution in d$^6$ DMSO (where d$^5$ DMSO=2.51δ)].

The starting material N-(5-bromo-4-(4-fluorophenyl)-6-isopropylpyrimidin-2-yl)-N-methylmethanesulfonamide was obtained as follows:
(i) A 5M to 6M solution of hydrogen chloride in isopropanol (38 mL, 194 mmoles) was added to a stirred mixture of urea (7.78 g, 129.6 mmoles) and 1-(4-fluorophenyl)-4-methylpentane-1,3-dione (8.43 g, 32.4 mmoles) in ethanol (49 mL). The reaction mixture was refluxed for 40 hours and then cooled to −6° C. The resultant precipitate was collected by filtration and washed with diethyl ether (20 mL). The solid was added to water (60 mL) and saturated aqueous sodium bicarbonate solution (10 mL). Further solid sodium bicarbonate (16.4 g, 195 mmoles) was added portionwise. The mixture was diluted with acetone (40 mL) and ethyl acetate (80 mL). The organic phase was separated and aqueous phase was extracted 2:1 ethyl acetate/acetone (3×120 mL). The organic phases were combined, washed with brine (30 mL), dried with anhydrous magnesium sulfate and concentrated in vacuo to yield 4.8 g of 4-(4-fluorophenyl)-6-isopropylpyrimidin-2-ol (64% yield); $^1$H NMR (400 MHz) (CDCl$_3$) δ TMS: 1.41 (6H, d, J=6.90 Hz), 3.08 (1H, m), 6.69 (1H, s), 7.17 (2H, dd, J=8.60 Hz, J=8.60 Hz), 8.14 (2H, dd, J=6.65 Hz, J=6.65 Hz), 13.57 (1H, br. s). Mp: 215-217° C. HRMS calculated for C$_{13}$H$_{13}$N$_2$OF. 232.1012, found 232.0963; used in subsequent reaction without further purification.

(ii) N-Bromosuccinimide (3.504 g, 19.69 mmoles) was added to suspension of 4-(4-fluorophenyl)-6-isopropylpyrimidin-2-ol (4.573 g, 19.69 mmoles) in DMF (30 mL) at −8.5° C. The mixture was stirred for 10 minutes and the reaction mixture was allowed to warm to ambient temperature. The mixture was stirred for 4 hours and then diluted with ethyl acetate (80 mL), toluene (20 mL), and water (100 mL). The organic phase was separated, and the aqueous phase extracted with 4:1 ethyl acetate/toluene (2×100 mL). The organic phases were combined and diluted with acetone (100 mL). The solution was washed with brine (75 mL), followed by saturated aqueous sodium bicarbonate (40 mL), and then concentrated in vacuo (with 3×40 mL toluene azeotropes) to yield 6.031 g of 5-bromo-4-(4-fluorophenyl)-6-isopropylpyrimidin-2-ol (98% yield); $^1$H NMR (400 MHz) (CDCl$_3$) δ TMS: 1.39 (6H, d, J=6.90 Hz), 3.57 (1H, m), 7.16 (2H, dd, J=8.60 Hz, J=8.60 Hz), 7.66 (2H, dd, J=8.70 Hz, J=5.40 Hz). Mp: Decomposes at 199° C. HRMS calculated for C$_{13}$H$_{12}$N$_2$OFBr 310.0117, found 310.0116; used in subsequent reaction without further purification.

(iii) Phosphoryl chloride (5.00 mL, 53.8 mmoles) was added to 5-bromo-4-(4-fluorophenyl)-6-isopropylpyrimidin-2-ol (5.027 g, 15.28 mmoles) and the reaction mixture was heated to an internal temperature of 90° C. The mixture was then stirred for 150 minutes at this temperature, then allowed to cool to 25° C. The reaction mixture was quenched by dropwise addition (with 30 mL of EtOAc rinses) into a stirred mixture of ice (60 g), water (40 mL), and sodium bicarbonate (10 g). After completion of the addition, sodium bicarbonate (13 g) added to assure neutrality. The mixture was then extracted with ethyl acetate (4×70 mL). The organic phases were combined and dried with anhydrous magnesium sulphate. The solution was filtered through a pad of diatomaceous earth, and concentrated in vacuo to yield 5-bromo-2-chloro-4-(4-fluorophenyl)-6-isopropylpyrimidine (4.98 g, 99% yield); $^1$H NMR (400 MHz) (CDCl$_3$) δ TMS: 1.34 (6H, d, J=6.70 Hz), 3.64 (1H, m), 7.17 (2H, dd, J=8.65 Hz, J=8.65 Hz), 7.73 (2H, dd, J=8.80 Hz, J=5.20 Hz). Mp: 99-101° C. HRMS calculated for C$_{13}$H$_{11}$N$_2$FClBr 327.9778, found 327.9752; used in subsequent reaction without further purification.

(iv) Sodium hydride (1.20 g, 30.0 mmol, 60% suspension in mineral oil) was washed with hexane (2×10 mL), and DMF (50 mL) was then added, followed by 5-bromo-2-chloro-4-(4-fluorophenyl)-6-isopropylpyrimidine (4.944 g, 15.0 mmoles). The resulting suspension was cooled to −7° C. and N-methylmethanesulfonamide (2.585 g, 22.5 mmoles) was added, washed in with DMF (10 mL). The mixture was stirred for 17.5 hours, then diluted with ethyl acetate (80 mL), toluene (100 mL), and water (120 mL). The organic phase was separated, and the aqueous phase was extracted with a mixture of ethyl acetate (20 mL) and toluene (30 mL). The organic phases were combined, washed with water (2×40 mL) and then brine (20 mL), and dried over anhydrous magnesium sulphate. The solution was concentrated in vacuo (with two 20 mL hexane azeotropes) to yield N-(5-bromo-4-(4-fluorophenyl)-6-isopropylpyrimidin-2-yl)-N-methylmethanesulfonamide (5.50 g, 91% yield); $^1$H NMR (400 MHz) (CDCl$_3$) δ TMS: 1.32 (6H, d, J=6.60 Hz), 3.49 (3H, s), 3.55 (3H, s), 3.63 (1H, m), 7.16 (2H, dd, J=8.65 Hz, J=8.65 Hz), 7.77 (2H, dd, J=8.70 Hz, J=5.30 Hz). Mp: 122-125° C. HRMS calculated for C$_{13}$H$_{17}$N$_3$O$_2$FSBr 401.0209, found 401.0225; used in subsequent reaction without further purification.

An alternative route to N-(5-bromo-4-(4-fluorophenyl)-6-isopropylpyrimidin-2-yl)-N-methylmethanesulfonamide is as follows:

4-(4-Fluorophenyl)-6-isopropylpyrimidin-2-ol

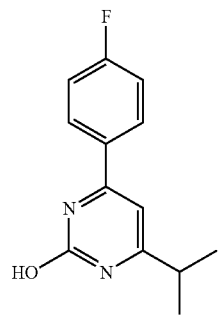

The reactor used for this experiment was thoroughly dried by carrying out a toluene distillation prior to use. Fresh toluene (100 mL) and potassium tert-butoxide (7.50 g, 64.8 mmol) were charged to the vessel and stirred to form a slurry. The mixture was cooled to −9° C. and 3-methyl-2-butanone (3.63 g, 41.7 mmol) added. The mixture was warmed to −5° C. and stirred for 30 mins. Ethyl-4-fluorobenzoate (6.25 g, 36.8 mmol) was dissolved in toluene (4 mL) and added via a syringe followed by a small toluene (1 ml) line wash. The mixture was stirred for 10 minutes at 0° C., warmed to 10° C., and then stirred at this temperature overnight. The mobile slurry was warmed to 25° C. and acetic acid (4.4 mL) added, followed by water (37.5 mL). The mixture was stirred thoroughly for 5 minutes and then allowed to stand. The lower phase was run off and discarded. A 5% sodium bicarbonate solution (16 mL) was charged to the upper phase, stirred for 5 minutes and then allowed to stand. The lower aqueous layer was run off and the upper organic phase washed twice with water (5 mL).

The remaining toluene solution was dried by azeotropic distillation (refluxing with Dean-Stark trap in place) and the solution cooled to 60° C. Urea (5.1 g, 84.9 mmol) and isopropanol (20 mL) were charged and stirred vigorously during the addition of hydrochloric acid (5 to 6 M in isopropanol, 32.3 mL, 183 mmol). The solution was heated to 80° C. and stirred for 48.5 hours before charging more hydrochloric acid in isopropanol (2 mL, 11 mmol). After a total of 112 hours at 80° C., the mixture was cooled to 60° C. and water (50 mL) added. After stirring for 15 minutes, the mixture was allowed to stand and the lower aqueous phase run off and retained. The aqueous phase was stirred and sodium hydrogen carbonate (6.9 g) added portion wise until pH=7. The product crystallised from solution and was then cooled to 20° C. The solid was filtered off and washed twice with water (20 mL) and dried in a vacuum oven at 50° C. overnight. 4-(4-fluorophenyl)-6-isopropylpyrimidin-2-ol (4.92 g) was isolated as a white powder in 56% overall yield; $^1$H NMR (400 MHz; CDCl$_3$) δ: 1.41 (6H, d), 3.08 (1H, m), 6.69 (1H, s), 7.17 (2H, dd), 8.14 (2H, dd), 13.57 (1H, br. s). Mp: 215-217° C. HRMS calculated for $C_{13}H_{13}N_2OF$ 232.1012, found 232.0963; used in subsequent reaction without further purification.

5-Bromo-4-(4-fluorophenyl)-6-isopropylpyrimidin-2-ol

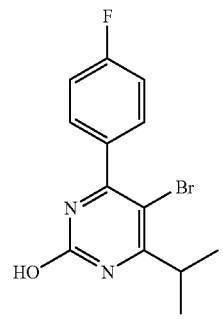

4-(4-Fluorophenyl)-6-isopropylpyrimidin-2-ol (8.00 g, 34.1 mmol) was charged to a reactor followed by DMF (100 mL). The suspension was stirred, cooled to −3° C. and N-bromosuccinimide (6.25 g, 34.8 mmol) added. The reaction mixture was warmed to 20° C. and stirred overnight. Water (100 mL) was charged to the reaction mixture and the crystalline mixture stirred for 1 hour before filtering off. The isolated solid was washed twice with water (25 mL) and the solid dried in a vacuum oven at 50° C. 5-Bromo-4-(4-fluorophenyl)-6-isopropylpyrimidin-2-ol (10.45 g, 97% yield) was obtained as a white solid;
$^1$H NMR (400 MHz; CDCl$_3$) δ: 1.39 (6H, d), 3.57 (1H, m), 7.16 (2H, dd), 7.66 (2H, dd). Mp: Decomposes at 199° C. HRMS calculated for $C_{13}H_{12}N_2OFBr$ 310.0117, found 310.0116; used in subsequent reaction without further purification.

N-(5-Bromo-4-(4-fluorophenyl)-6-isopropylpyrimidin-2-yl)-N-methylmethanesulfonamide

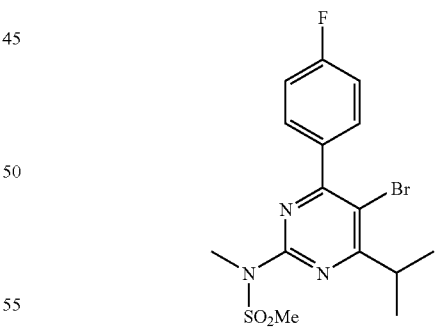

5-Bromo-4-(4-fluorophenyl)-6-isopropylpyrimidin-2-ol (62.2 g, 199 mmol), potassium carbonate (35.83 g, 259 mmol) and butyl acetate (435.4 mL) were charged to a 2 L multi-neck flask and stirred/heated to 42° C. p-Toluenesulfonyl chloride (41.83 g, 219 mmol) was then added in portions over 50 minutes, maintaining the temperature at ≦45° C. The reaction was stirred at this temp for 2.5 hours, at which point LCMS showed only the desired intermediate (MH$^+$=467) present. Potassium carbonate (41.25 g, 299 mmol) and butyl acetate (186.6 mL) were then added and reaction heated to 120° C. Once at this temperature N-methylmethanesulfonamide (28.21 g, 259 mmol) was added over 30 mins. The reaction was held at this temperature for 18 hours, then butyl acetate (330 mL) and water (412 mL) were added, reducing the reaction temperature to 75° C. Stirring was continued at this temperature for 20 minutes, then the reaction mixture was transferred to a separating funnel, and allowed to stand for 10 mins to separate. The aqueous layer was separated off and re-extracted with butyl acetate (250 mL) by stirring at 60° C. for 15 mins. The organic layers were combined and 1 M aqueous NaOH (330 mL) added. This mixture was stirred at 60° C. for 20 minutes, then the lower aqueous phase separated off. The organic layer was concentrated in vacuo to 20% original volume, then allowed to cool and crystallize. The crude solid was isolated by filtration (50.5 g slightly damp), and this material recrystallized from methanol (500 mL), filtered and dried at 50° C. to constant weight to give the title compound (30.54 g, 38% yield) as a white crystalline solid.

$^1$H NMR (400 MHz; CDCl$_3$) δ: 1.32 (6H, d), 3.49 (3H, s), 3.55 (3H, s), 3.63 (1H, m), 7.16 (2H, dd), 7.77 (2H, dd). Mp: 122-125° C. HRMS calculated for C$_{13}$H$_{17}$N$_3$O$_2$FSBr 401.0209, found 401.0225.

The invention claimed is:

1. A process for the manufacture of a compound of formula I

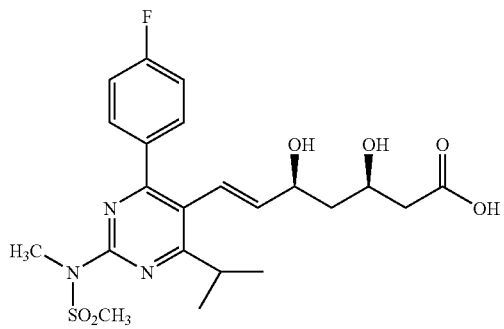

or a pharmaceutically acceptable salt thereof,
which comprises reacting a compound of formula II,

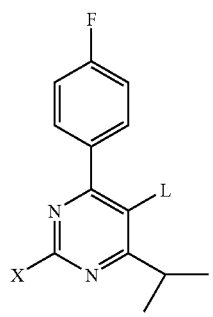

wherein
L is a leaving group and
X is a group Z which is N-(methyl)methylsulfonylamino (CH$_3$SO$_2$N(CH$_3$)—);

with a compound of the formula III,

wherein
A is selected from a group (i) to (vii) below,

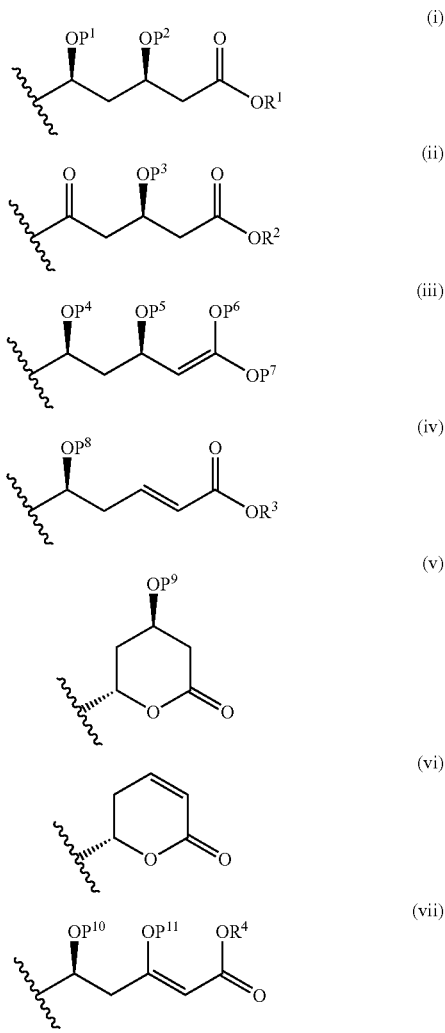

wherein P$^1$ and P$^2$ are independently selected from hydrogen and a hydroxy protecting group, or
P$^1$ together with P$^2$ form a 1,3-dihydroxy protecting group;
P$^3$ is hydrogen or a hydroxy protecting group;
P$^4$ and P$^5$ are independently selected from hydrogen and a hydroxy protecting group, or P$^4$ together with P$^5$ form a 1,3-dihydroxy protecting group, and
P$^6$ and P$^7$ are independently a hydroxy protecting group; or P$^5$ together with P$^6$ form a 1,3-dihydroxy protecting group, and P$^4$ is hydrogen or a hydroxy protecting group and P$^7$ is a hydroxy protecting group;
P$^8$ is hydrogen or a hydroxy protecting group;
P$^9$ is hydrogen or a hydroxy protecting group;
P$^{10}$ and P$^{11}$ are independently selected from hydrogen and a hydroxy protecting group, or P$^{10}$ together with P$^{11}$, or P$^{11}$ together with R$^4$, form a 1,3-dihydroxy protecting group;
and unless otherwise stated R$^1$, R$^2$, R$^3$ and R$^4$ are independently carboxy protecting groups;

in the presence of a catalytically effective amount of a palladium catalyst and in the presence of a base;
followed by
(a) when A is a group (i), carrying out in any order the steps of (1) when $P^1$ is a hydroxy protecting group, removal of the protecting group $P^1$; (2) when $P^2$ is a hydroxy protecting group, removal of the protecting group $P^2$; and (3) removal of the protecting group $R^1$;
(b) when A is a group (ii), carrying out in any order the steps of (1) asymmetric reduction of the carbonyl group adjacent to the carbon-carbon double bond; (2) when $P^3$ is a hydroxy protecting group, removal of the protecting group $P^3$; and (3) removal of the protecting group $R^2$;
(c) when A is a group (iii), carrying out in any order the steps of (1) when $P^4$ is a hydroxy protecting group, removal of the protecting group $P^4$; (2) when $P^5$ is a hydroxy protecting group, removal of the protecting group $P^5$; (3) removal of the protecting group $P^6$; and (4) removal of the protecting group $P^7$;
(d) when A is a group (iv), carrying out in any order the steps of (1) when $P^8$ is a hydroxy protecting group, removal of the protecting group $P^8$; (2) asymmetric hydration of the carbon-carbon double bond adjacent to the ester group $COOR^3$; and (3) removal of the protecting group $R^3$;
(e) when A is a group (v), carrying out in any order the steps of (1) when $P^9$ is a hydroxy protecting group, removal of the protecting group $P^9$; and (2) hydrolysis under basic conditions;
(f) when A is a group (vi), carrying out in any order the steps of (1) asymmetric hydration of the ring carbon-carbon double bond; and (2) hydrolysis under basic conditions; and
(g) when A is a group (vii), carrying out in any order the steps of (1) asymmetric reduction of the carbon-carbon double bond adjacent to the group $COOR^4$; (2) when $P^{10}$ is a hydroxy protecting group, removal of the protecting group $P^{10}$; (3) when $P^{11}$ is a hydroxy protecting group, removal of the protecting group $P^{11}$; and (4) removal of the protecting group $R^4$;
whereafter, when the product is obtained in the free acid form, optionally forming a pharmaceutically acceptable salt of the compound of formula I, or when the product is obtained as a salt, optionally converting the product to a different pharmaceutically acceptable salt.

2. The process as claimed in claim 1 wherein A is the group (i) as defined in claim 1.

3. A process for the manufacture of a compound of the formula IV

IV wherein $P^1$ and $P^2$ are independently hydroxy-protecting groups, or $P^1$ together with $P^2$ form a 1,3-dihydroxy protecting group, X is the group Z as defined in claim 1, and $R^1$ is a carboxy protecting group, which comprises reacting a compound of the formula II as defined in claim 1 wherein X is the group Z as defined in claim 1 and L is a leaving group, with a compound of the formula III as defined in claim 1 wherein A is a group (i) as defined in claim 1 and $P^1$ and $P^2$ are independently hydroxy-protecting groups, or $P^1$ together with $P^2$ form a 1,3-dihydroxy protecting group, and $R^1$ is a carboxy protecting group, in the presence of a catalytically effective amount of a palladium catalyst and in the presence of a base.

4. A process for the manufacture of a compound of the formula V

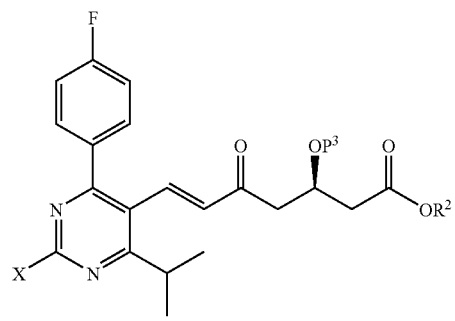

wherein $P^3$ is hydrogen or a hydroxy-protecting group, X is the group Z as defined in claim 1, and $R^2$ is a carboxy protecting group comprising reacting a compound of the formula II as defined in claim 1 wherein X is the group Z as defined in claim 1 and L is a leaving group with a compound of the formula III as defined in claim 1 in which A is a group (ii) as defined in claim 1 wherein $P^3$ is a hydrogen or a hydroxy-protecting group and $R^2$ is a carboxy protecting group, in the presence of a catalytically effective amount of a palladium catalyst and in the presence of a base.

5. A process for the manufacture of a compound of the formula VI

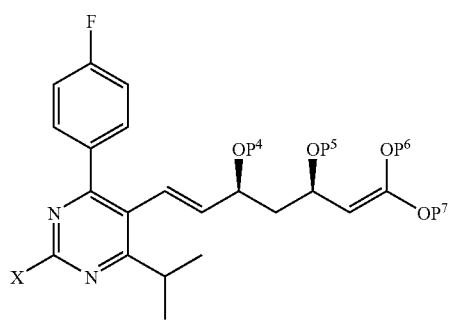

wherein $P^4$, $P^5$, $P^6$ and $P^7$ are independently hydroxy-protecting groups, or $P^4$ together with $P^5$ or $P^5$ together with $P^6$ form a 1,3-dihydroxy protecting group, and X is the group Z as defined in claim 1, comprising reacting a compound of the formula II as defined in claim 1 wherein X is the group Z as defined in claim 1 and L is a leaving group, with a compound of the formula III as defined in claim 1 in which A is a group (iii) as defined in claim 1 wherein $P^4$, $P^5$, $P^6$ and $P^7$ are independently hydroxy-protecting groups, or $P^4$ together with $P^5$ or $P^5$ together with $P^6$ form a 1,3-dihydroxy protecting group, in the presence of a catalytically effective amount of a palladium catalyst and in the presence of a base.

6. A process for the manufacture of a compound of the formula VII

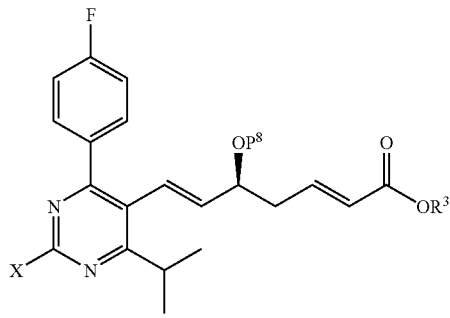

wherein $P^8$ is a hydroxy-protecting group, X is the group Z as defined in claim 1, and $R^3$ is a carboxy protecting group comprising reacting a compound of the formula II as defined in claim 1 wherein X is the group Z as defined in claim 1 and L is a leaving group with a compound of the formula III as defined in claim 1 in which A is a group (iv) as defined in claim 1 wherein $P^8$ is a hydroxy-protecting group and $R^3$ is a carboxy protecting group, in the presence of a catalytically effective amount of palladium catalyst and in the presence of a base.

7. A process for the manufacture of a compound of the formula VIII

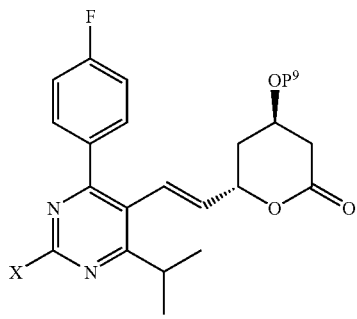

wherein $P^9$ is hydrogen or a hydroxy-protecting group and X is the group Z as defined in claim 1, comprising reacting a compound of the formula II as defined in claim 1 wherein X is the group Z as defined in claim 1 and L is a leaving group with a compound of the formula III as defined in claim 1 in which A is a group (v) as defined in claim 1 wherein $P^9$ is a hydroxy-protecting group, in the presence of a catalytically effective amount of a palladium catalyst and in the presence of a base.

8. A process for the manufacture of a compound of the formula IX

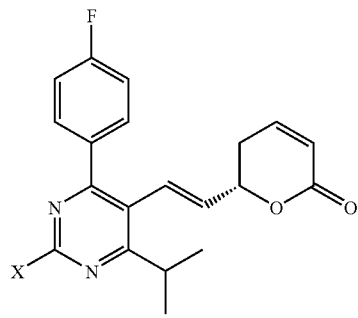

wherein X is the group Z as defined in claim 1, comprising reacting a compound of the formula II as defined in claim 1 wherein X is the group Z as defined in claim 1 and L is a leaving group with a compound of the formula III as defined in claim 1 in which A is a group (vi) as defined in claim 1, in the presence of a catalytically effective amount of a palladium catalyst and in the presence of a base.

9. A process for the manufacture of a compound of the formula X

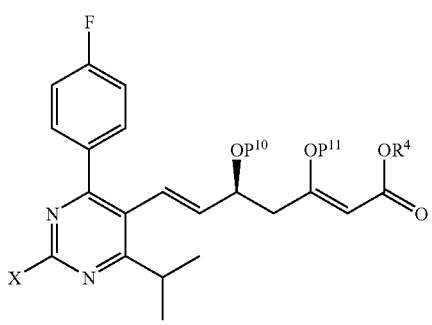

wherein $P^{10}$ and $P^{11}$ are independently selected from hydrogen and a hydroxy protecting group, or $P^{10}$ together with $P^{11}$, or $P^{11}$ together with $R^4$, form a 1,3-dihydroxy protecting group; X is the group Z as defined in claim 1; and $R^4$ is a carboxy protecting group comprising reacting a compound of the formula II as defined in claim 1 wherein X is the group Z as defined in claim 1 and L is a leaving group, with a compound of the formula III as defined in claim 1 in which A is a group (vii) as defined in claim 1 wherein $P^{10}$ and $P^{11}$ are independently selected from hydrogen and a hydroxy protecting group, or $P^{11}$ together with $P^{11}$ form a 1,3-dihydroxy protecting group, in the presence of a catalytically effective amount of a palladium catalyst and in the presence of a base.

10. The process as claimed in any of claim 1 or 3-9 wherein the palladium catalyst is bis(tri-tert-butylphosphine)palladium (0).

11. The process as claimed in any of claim 1 or 3-9 wherein the base is ammonia or a bulky tertiary amine.

12. The process as claimed in any of claim 1 or 3-9 wherein the reaction is carried out in a solvent selected from water, water and N,N-dimethylformamide and water and N,N-dimethylacetamide.

* * * * *